US008865708B2

(12) United States Patent
Deshaies et al.

(10) Patent No.: US 8,865,708 B2
(45) Date of Patent: Oct. 21, 2014

(54) METHODS AND COMPOSITIONS FOR INHIBITION OF THE TRANSITIONAL ENDOPLASMIC RETICULUM ATPASE

(75) Inventors: Raymond J. Deshaies, Claremont, CA (US); Tsui-Fen Chou, Pasadena, CA (US); Frank J. Schoenen, Lawrence, KS (US); Kelin Li, Lawrence, KS (US); Kevin J. Frankowski, Lawrence, KS (US); Jeffrey Aube, Lawrence, KS (US); Samuel W. Gerritz, Guilford, CT (US); Han-Jie Zhou, Foster City, CA (US)

(73) Assignees: California Institute of Technology, Pasadena, CA (US); The University of Kansas, Lawrence, KS (US); Cleave Biosciences, Inc., Burlingame, CA (US)

( * ) Notice: Subject to any disclaimer, the term of this patent is extended or adjusted under 35 U.S.C. 154(b) by 0 days.

(21) Appl. No.: 13/103,003

(22) Filed: May 6, 2011

(65) Prior Publication Data

US 2011/0288082 A1 Nov. 24, 2011

Related U.S. Application Data

(60) Provisional application No. 61/332,667, filed on May 7, 2010.

(51) Int. Cl.
| | | |
|---|---|---|
| *A61K 31/54* | (2006.01) | |
| *A61K 31/535* | (2006.01) | |
| *A61K 31/538* | (2006.01) | |
| *A61K 31/517* | (2006.01) | |
| *A61K 31/4184* | (2006.01) | |
| *C12Q 1/42* | (2006.01) | |
| *A61K 31/53* | (2006.01) | |
| *C12Q 1/48* | (2006.01) | |

(52) U.S. Cl.
CPC .......... *A61K 31/517* (2013.01); *G01N 2500/02* (2013.01); *A61K 31/538* (2013.01); *A61K 31/4184* (2013.01); *C12Q 1/42* (2013.01); *A61K 31/53* (2013.01); *C12Q 1/485* (2013.01)
USPC ................ 514/230.5; 514/249; 514/266.2; 514/266.21; 514/394; 514/266.4; 514/245; 544/73; 544/291; 544/105; 544/284; 506/11; 435/18

(58) Field of Classification Search
USPC ......... 514/230.5, 249, 266.2, 266.23, 266.21, 514/394, 266.4, 245; 544/73, 291, 105, 544/284; 506/11; 435/18
See application file for complete search history.

(56) References Cited

U.S. PATENT DOCUMENTS

2006/0025406 A1* 2/2006 Zembower et al. ........... 514/218
2009/0253717 A1 10/2009 Brown et al.

FOREIGN PATENT DOCUMENTS

| CN | 103068393 A | 4/2013 |
|---|---|---|
| JP | 2013530942 A | 8/2013 |
| WO | WO-9214716 A1 | 9/1992 |
| WO | WO-03055866 A1 | 7/2003 |
| WO | WO-2004030672 A1 | 4/2004 |
| WO | WO-2006014420 A1 | 2/2006 |
| WO | WO-2006105056 A2 | 10/2006 |
| WO | WO-2007041282 A2 | 4/2007 |
| WO | WO-2008157500 A1 | 12/2008 |
| WO | WO 2009001060 A2 * | 12/2008 |
| WO | WO-2009011910 A2 | 1/2009 |
| WO | WO-2010003908 A1 | 1/2010 |
| WO | WO-2011140527 A2 | 11/2011 |

OTHER PUBLICATIONS

"International Application Serial No. PCT/US2011/035654, International Preliminary Report on Patentability mailed Nov. 22, 2012", 7 pgs.
"International Application Serial No. PCT/US2011/035654, Search Report mailed Jan. 19, 2012", 4 pgs.
"International Application Serial No. PCT/US2011/035654, Written Opinion mailed Jan. 19, 2012", 5 pgs.
European Application Serial No. 11778469.4, Extended European Search Report mailed Feb. 13, 2014, 11 pgs.
Chou, et al., "Reversible inhibitor of p97, DBeQ, impairs both ubiquitin-dependent and autophagic protein clearance pathways", Proceedings of The National Academy of Sciences of The United States of America, vol. 108, No. 12, (Mar. 22, 2011), 4834-4839.
Wang, Q, et al., "Inhibition of p97-dependent protein degradation by Eeyarestatin I", Journal of Biological Chemistry, vol. 283, No. 12, (Mar. 2008), 7445-7454.
Wang, Qiuyan, et al., "The ERAD Inhibitor Eeyarestatin I is a Bifunctional Compound with a Membrane-Binding Domain and a p97/VCP Inhibitory Group", Plos One, vol. 5, No. 11, (Nov. 2010), 1-12.
Australian Serial No. 2011249859, First Examiner Report mailed Sep. 3, 2013, 4 pgs.
Chinese Application Serial No. 201180026946.X, Office Action mailed Jan. 6, 2014, 8 pgs.
Australian Application Serial No. 2011249859, Response filed Jun. 4, 2014 to Office Action mailed Sep. 4, 2013, 51 pgs.
Chinese Application Serial No. 201180026946.X, Response filed May 6, 2014 to Office Action mailed Jan. 6, 2014, w/English Claims, 45 pgs.

* cited by examiner

Primary Examiner — Wu-Cheng Winston Shen
Assistant Examiner — Jean Cornet
(74) Attorney, Agent, or Firm — Schwegman Lundberg & Woessner, P.A.

(57) ABSTRACT

Compounds of Formulas I-XLIII are identified as direct inhibitors of p97 ATPase or of the degradation of a p97-dependent ubiquitin-proteasome system (UPS) substrate. Methods and compositions are disclosed for inhibiting p97 ATPase and the degradation of a p97-dependent UPS substrate, and for identifying inhibitors thereof.

18 Claims, No Drawings

METHODS AND COMPOSITIONS FOR INHIBITION OF THE TRANSITIONAL ENDOPLASMIC RETICULUM ATPASE

CROSS-REFERENCE TO RELATED APPLICATION(S)

This application claims priority to and the benefit of U.S. Provisional Application Ser. No. 61/332,667, filed on May 7, 2010, the entire contents of which are incorporated herein by reference.

STATEMENT REGARDING FEDERALLY SPONSORED RESEARCH OR DEVELOPMENT

This invention was made with government support under MH085687 awarded by National Institutes of Health. The government has certain rights in the invention.

TECHNICAL FIELD

Embodiments of this invention are directed to selective inhibitors of the ubiquitin-proteasome system (UPS). In particular, inhibitors of the transitional endoplasmic reticulum (p97) ATPase and an ubiquitin substrate are identified.

TECHNICAL BACKGROUND

The ubiquitin-proteasome system (UPS) comprises one of the most important mechanisms for post-translational regulation of protein function in eukaryotic cells. The UPS comprises hundreds of enzymes that promote covalent attachment of ubiquitin and ubiquitin-like proteins (UBL) to target proteins, as well as enzymes that reverse the modification. Conjugation of ubiquitin to target proteins is a multi-step process (Weissman, 2001, *Nat. Rev. Mol. Cell. Biol.*, 2:169-178; Finley, 2009, *Annu. Rev. Biochem.*, 78:477-513; Schrader et al., 2009, *Nat. Chem. Biol.*, 5:815-822; Deshaies et al., 2009, *Annu. Rev. Biochem.*, 78: 399-434). The most intensively-studied consequence of ubiquitination is protein degradation. Given the importance of the UPS to regulatory biology there has been considerable interest in developing small molecule inhibitors as potential therapies for a range of human diseases. The UPS has been validated as an important target in cancer by clinical use of the proteasome inhibitor, bortezomib (Velcade), for the treatment of multiple myeloma and mantle cell lymphoma (Kane et al., 2003, *Oncologist*, 8:508-513; Colson et al., 2004, *Clin. J. Oncol. Nurs.*,8:473-480).

The AAA (ATPase associated with diverse cellular activities) ATPase p97 is conserved across all eukaryotes and is essential for life in budding yeast (Giaever et al., 2002, *Nature*, 418:387-391) and mice (Muller et al., 2007, *Biochem. Biophys. Res. Commun.*, 354:459-465). p97 (also referred to as the transitional endoplasmic reticulum ATPase) is overexpressed in several cancers supporting the idea that it could be a target of general importance in oncology (Yamamoto et al., 2004, *Clin. Cancer Res.*, 10:5558-5565; Yamamoto et al., 2003, *J. Clin. Oncol.*, 21:447-452). Elevated expression levels of p97 have been associated with poor prognosis of cancer (Yamamoto et al., 2004, *Ann. Surg. Oncol.* 11:697-704; Tsujimoto et al., 2004, *Clin. Cancer Res.*, 10:23007-3012). Additionally, p97 is an essential ATP hydrolase and thus, it should be druggable and have antiproliferative activity. Furthermore, p97 is essential for endoplasmic reticulum associated degradation (ERAD) (Ye et al., 2004, *Nature*, 429:841-847; Ye et al., 2003, *J. Cell Biol.*, 162:71-84; Neuber et al., 2005, *Nat. Cell Biol.*, 7:993-998). Blockade of ERAD is thought to be a key mechanism underlying the anti-cancer effects of bortezomib (Nawrocki et al., 2005, *Cancer Res.*, 65:11510-11519). Given that p97 is implicated in ERAD, but otherwise has a more restricted role in the UPS compared to the proteasome, it is possible that drugs that target p97 might retain much of the efficacy of bortezomib but with less toxicity.

SUMMARY

In one embodiment of the present invention, a method of decreasing p97 ATPase activity and/or degradation of a p97-dependent ubiquitin-proteasome system (UPS) substrate in a human cell, is provided, including administering to a human an effective amount of at least one of (i) a compound represented by any of Formulas I-VII, IX, XI-XLIII, (ii) a PEGylated analog of the compound, (iii) a pharmaceutically acceptable salt of said compound or analog, or (iv) an isomer of said compound, analog, or salt, wherein, for Formula I, $R^1$, $R^2$, $R^3$, $R^4$, and $R^5$ are selected from the combinations listed in Tables 1.1, 12.1, and 18.1; wherein, for Formula II, $R^1$ is selected from the groups listed in Tables 2.1, 13.1, and 19.1; wherein, for Formula III, $R^1$ is selected from the groups listed in Table 3.1; wherein, for Formula IV, $R^1$ is selected from the groups listed in Table 4.1; wherein, for Formula V, $R^1$ is selected from the groups listed in Table 5.1; wherein, for Formula VI, $R^1$ is selected from the groups listed in Tables 6.1 and 20.1; wherein, for Formula VII, $R^1$, n, X, and Y are selected from the combinations listed in Tables 7.1 and 14.1; wherein for Formula XI, $R^2$ is selected from the groups listed in Tables 9.1 and 21; wherein for Formula XII, $R^4$ is selected from the groups listed in Tables 10.1 and 22.1; wherein, for Formula XXI, R1 is 5,6-dimethyl; and wherein, for Formula XXV, $R^1$ is chlorine at position 3 and $R^2$ is selected from hydrogen and methoxy at position 4.

In one embodiment, the preceding method is provided wherein the compound decreases p97 ATPase activity and degradation of a p97-dependent UPS substrate in a human cell, and the compound is represented by any of Formulas I-VII, IX, and XI-XIX, wherein: for Formula I, $R^1$, $R^2$, $R^3$, $R^4$, and $R^5$ are selected from the combinations listed in Table 1.1, for Formula II, $R^1$ is selected from the groups listed in Table 2.1, for Formula III, $R^1$ is selected from the groups listed in Table 3.1, for Formula IV, $R^1$ is selected from the groups listed in Table 4.1, for Formula V, $R^1$ is selected from the groups listed in Table 5.1, for Formula VI, $R^1$ is selected from the groups listed in Table 6.1, for Formula VII, $R^1$, n, X, and Y are selected from the combinations listed in Table 7.1, for Formula XI, $R^2$ is selected from the groups listed in Table 9.1, and for Formula XII, $R^4$ is selected from the groups listed in Table 10.1.

In one embodiment, the preceding method is provided wherein the isomer is a regioisomer or a stereoisomer.

In one embodiment, a method of identifying an inhibitory compound that decreases p97 activity in a human cell is provided, including: (a) forming a p97 protein control solution; (b) forming a test solution comprising p97 protein and at least one of (i) a compound represented by any of Formulas LII through LXVI, (ii) a PEGylated, biotinylated, or fluorescently labeled analog of the compound, (iii) a pharmaceutically acceptable salt of said compound or analog, or (iv) an isomer of said compound analog, or salt; (c) measuring p97 activity of the control solution and of the test solution in the presence of ATP and a kinase; and (d) comparing the measured activities, wherein for Formula LII, n is selected from 0, 1, and 2; wherein, for Formula LIII, $R^1$ and $R^2$ are independently selected from hydrogen, methyl, ethyl, propyl and butyl; wherein, for Formula LIV, $R^1$ is selected from hydrogen, methyl, fluorine, chlorine, bromine, and OMe (methoxy), and $R^2$ is selected from hydrogen, methyl, ethyl, propyl, and butyl; wherein, for Formula LV, $R^1$ is selected from hydrogen, methyl, fluorine, chlorine, bromine, and OMe (methoxy), and $R^2$ is selected from hydrogen, methyl, ethyl, propyl, and butyl; wherein, for Formula LVI, $R^1$ and $R^2$ are independently selected from hydrogen, methyl, fluorine, chlorine, bromine, and OMe (methoxy); wherein, for Formula LVII, X is oxygen, NMe (nitrogen-methyl), NEt (nitrogen-ethyl), NPh (nitrogen-phenyl); n is selected from −1, 0, 1, and 2; m is selected from 1, 2, 3, and 4; and $R^1$ and $R^2$ are independently selected from hydrogen, methyl, fluorine, chlorine, bromine and methoxy; wherein, for Formula LVIII, X is selected from oxygen, NMe (nitrogen-methyl), NEt (nitrogen-ethyl), and NPh (nitrogen-phenyl); n is selected from −1, 0, 1, and 2; m is selected from 1, 2, 3, and 4; and $R^1$ is selected from hydrogen, methyl, fluorine, chlorine, bromine, and methoxy; wherein, for Formula LIX, $R^1$, $R^2$ and $R^3$ are independently selected from hydrogen, $A(CH_2)_nCH_3$, and $A(CH_2)_nX$, where n is selected from 0, 1, 2, 3, 4 and 5, A is O, S or NH and X is selected from heteroaryl, O(alkyl), S(alkyl), (O-alkyl)$_2$, and (S-alkyl)$_2$; wherein, for Formula LX, $A^1$ is selected from O, S, Se, N, NH, CH, $CH_2$, CHalkyl, and Calkyl, wherein n is 1 or 2; $A^2$ is selected from N, NH, CH, and Calkyl; and $R^1$ is selected from H, $A(CH_2)_nCH_3$, or $A(CH_2)_nX$, where A is O, S or NH and X is heteroaryl, O(alkyl), S(alkyl), (O-alkyl)$_2$, or (S-alkyl)$_2$; and n is 0, 1, 2, 3, 4, or 5; wherein, for Formula LXI, $R^1$, $R^2$ and $R^3$ are independently selected from alkyl, alkoxyalkyl, and aminoalkyl; wherein, for Formula LXII; n is selected from −1, 0, 1, and 2; m is selected from 0, 1, and 2; and X is selected from $CH_2$, O, NMe, NEt, and NPh; wherein, for Formula LXIII, $R^1$ and $R^2$ are independently selected from H, Me, Et, Pr, and Bu; X is selected from $CH_2$, O, NMe, NEt, and NPh; and n is selected from −1, 0, 1 and 2; wherein, for Formula LXIV, $R^1$ is selected from H, Me, F, Cl, Br, and OMe; $R^2$ is selected from H, Me, Et, Pr, and Bu; X is selected from $CH_2$, O, NMe, NEt, and NPh; and n is selected from −1, 0, 1, and 2; wherein, for Formula LXV, $R^1$ is selected from H, Me, F, Cl, Br, and OMe; $R^2$ is selected from H, Me, Et, Pr, and Bu; X is selected from $CH_2$, O, NMe, NEt, and NPh; and n is selected from −1, 0, 1, and 2; and, wherein, for Formula LXVI, $R^1$ and $R^2$ are independently selected from H, Me, F, Cl, Br, and OMe; X is selected from CH2, O, NMe, NEt, and NPh; and n is selected from −1, 0, 1, and 2.

In one embodiment, the preceding composition is provided wherein the isomer is a regioisomer or a stereoisomer.

In one embodiment, a composition for decreasing p97 ATPase activity and/or degradation of a p97-dependent UPS substrate is provided, including: at least one of (i) a compound selected from any of Formulas II-VII, IX, XI, XII, XX, XXI, XXIV, XXV, XLII, and XLIII, (ii) a PEGylated, biotinylated, or fluorescently labeled analog of the compound, (iii) a pharmaceutically acceptable salt of said compound or analog; or (iv) an isomer of said compound analog, or salt, wherein, for Formula II, $R^1$ is selected from the groups listed in Tables 2.2, 13.1, and 19.1; wherein, for Formula III, $R^1$ is selected from the groups listed in Table 3.1; wherein, for Formula IV, $R^1$ is selected from the groups listed in Table 4.1; wherein, for Formula V, $R^1$ is selected from the groups listed in Table 5.1; wherein, for Formula VI, $R^1$ is selected from the groups listed in Tables 6.1 and 20.1; wherein, for Formula VII, R', n, X, and Y are selected from the combinations listed in Tables 7.1 and 14.1; wherein, for Formula XI, $R^2$ is selected from the groups listed in Tables 9.1 and 21; wherein, for Formula XII, $R^4$ is selected from the groups listed in Tables 10.1 and 22.1; and wherein, for Formula XXV, $R^1$ is chlorine at position 3 and $R^2$ is selected from hydrogen and methoxy at position 4.

In one embodiment, the preceding composition for decreasing p97 ATPase activity and/or degradation of a p97-dependent UPS substrate is provided further including a pharmaceutically acceptable carrier.

In one embodiment, the preceding composition for decreasing p97 ATPase activity and/or degradation of a p97-dependent UPS substrate is provided, wherein the isomer is a regioisomer or a stereoisomer.

In one embodiment, the preceding composition decreases p97 ATPase activity and degradation of a p97-dependent UPS substrate, and the compound is represented by any of Formulas II-VII, IX, XI, and XII, wherein, for Formula II, $R^1$ is selected from the groups listed in Table 2.2; for Formula III, $R^1$ is selected from the groups listed in Table 3.1; for Formula IV, $R^1$ is selected from the groups listed in Table 4.1; for Formula V, $R^1$ is selected from the groups listed in Table 5.1; for Formula VI, $R^1$ is selected from the groups listed in Table 6.1; for Formula VII, $R^1$, n, X, and Y are selected from the combinations listed in Table 7.1; for Formula XI, $R^2$ is selected from the groups listed in Table 9.1; and for Formula XII, $R^4$ is selected from the groups listed in Table 10.1.

In one embodiment, the preceding composition that decreases p97 ATPase activity and degradation of a p97-dependent UPS substrate is provided, further including a pharmaceutically acceptable carrier.

In one embodiment, the preceding composition that decreases p97 ATPase activity and degradation of a p97-dependent UPS substrate is provided, wherein the isomer is a regeoisomer or a stereoisomer.

In one embodiment, a composition for identifying an inhibitor that decreases p97 ATPase activity and/or degradation of a p97-dependent UPS substrate is provided, including: at least one of (i) a compound selected from any of Formulas LII-LXVI, (ii) a PEGylated, biotinylated, or fluorescently labeled analog of the compound, (iii) a pharmaceutically acceptable salt of said compound or analog; or (iv) a isomer of said compound, analog, or salt: wherein for Formula LII, n is selected from 0, 1, and 2; wherein, for Formula LIII, $R^1$ and $R^2$ are independently selected from hydrogen, methyl, ethyl, propyl and butyl; wherein, for Formula LIV, $R^1$ is selected from hydrogen, methyl, fluorine, chlorine, bromine, and OMe (methoxy), and $R^2$ is selected from hydrogen, methyl, ethyl, propyl, and butyl; wherein, for Formula LV, $R^1$ is selected from hydrogen, methyl, fluorine, chlorine, bromine, and OMe (methoxy), and $R^2$ is selected from hydrogen, methyl, ethyl, propyl, and butyl; wherein, for Formula LVI, $R^1$ and $R^2$ are independently selected from hydrogen, methyl, fluorine, chlorine, bromine, and OMe (methoxy); wherein, for Formula LVII, X is oxygen, NMe (nitrogen-methyl), NEt (nitrogen-ethyl), NPh (nitrogen-phenyl); n is selected from −1, 0, 1, and 2; m is selected from 1, 2, 3, and 4; and $R^1$ and $R^2$ are independently selected from hydrogen, methyl, fluorine, chlorine, bromine and methoxy; wherein, for Formula LVIII, X is selected from oxygen, NMe (nitrogen-methyl), NEt (nitrogen-ethyl), and NPh (nitrogen-phenyl); n is selected from −1, 0, 1, and 2; m is selected from 1, 2, 3, and 4; and $R^1$ is selected from hydrogen, methyl, fluorine, chlorine, bromine, and methoxy; wherein, for Formula LIX, $R^1$, $R^2$ and $R^3$ are independently selected from hydrogen, $A(CH_2)_nCH_3$, and $A(CH_2)_nX$, where n is selected from 0, 1, 2, 3, 4 and 5, A is O, S or NH and X is selected from heteroaryl, O(alkyl), S(alkyl), (O-alkyl)$_2$, and (S-alkyl)$_2$; wherein, for Formula LX, A$^1$ is selected from O, S, Se, N, NH, CH, CH$_2$, CHalkyl, and Calkyl, wherein n is 1 or 2; A$^2$ is selected from N, NH, CH, and Calkyl; and R$^1$ is selected from H, A(CH$_2$)$_n$CH$_3$, or A(CH$_2$)$_n$X, where A is O, S or NH and X is heteroaryl, O(alkyl), S(alkyl), (O-alkyl)$_2$, or (S-alkyl)$_2$; and n is 0, 1, 2, 3, 4, or 5; wherein, for Formula LXI, R$^1$, R$^2$ and R$^3$ are independently selected from alkyl, alkoxyalkyl, and aminoalkyl; wherein, for Formula LXII; n is selected from −1, 0, 1, and 2; m is selected from 0, 1, and 2; and X is selected from CH$_2$, O, NMe, NEt, and NPh; wherein, for Formula LXIII, R$^1$ and R$^2$ are independently selected from H, Me, Et, Pr, and Bu; X is selected from CH$_2$, O, NMe, NEt, and NPh; and n is selected from −1, 0, 1 and 2; wherein, for Formula LXIV, R$^1$ is selected from H, Me, F, Cl, Br, and OMe; R$^2$ is selected from H, Me, Et, Pr, and Bu; X is selected from CH$_2$, O, NMe, NEt, and NPh; and n is selected from −1, 0, 1, and 2; wherein, for Formula LXV, R$^1$ is selected from H, Me, F, Cl, Br, and OMe; R$^2$ is selected from H, Me, Et, Pr, and Bu; X is selected from CH$_2$, O, NMe, NEt, and NPh; and n is selected from −1, 0, 1, and 2; and, wherein, for Formula LXVI, R$^1$ and R$^2$ are independently selected from H, Me, F, Cl, Br, and OMe; X is selected from CH$_2$, O, NMe, NEt, and NPh; and n is selected from −1, 0, 1, and 2.

In one embodiment, the preceding composition for identifying an inhibitor is provided, further including a pharmaceutically acceptable carrier.

In one embodiment, the preceding composition for identifying an inhibitor is provided, wherein the isomer is a regeoisomer or a stereoisomer.

In one embodiment, a method of decreasing p97 ATPase activity and/or degradation of a p97-dependent ubiquitin-proteasome system (UPS) substrate in a human cell is provided, including: administering to a human an effective amount of at least one of (i) a compound represented by any of Formulas VIII, X, XI, and XII, (ii) a PEGylated analog of the compound, (iii) a pharmaceutically acceptable salt of said compound or analog; or (iv) an isomer of said compound, analog, or salt, wherein, for Formula XI, R$^2$ is selected from the groups listed in Tables 9.2 and 15.1; and wherein, for Formula XII, R$^4$ is selected from the groups listed in Tables 10.2 and 22.2.

In one embodiment, a composition for decreasing p97 ATPase activity and/or degradation of a p97-dependent UPS substrate is provided, including at least one of (i) a compound selected from any of Formulas VIII, X, XI, XII, (ii) a PEGylated, biotinylated, or fluorescently labeled analog of the compound, (iii) a pharmaceutically acceptable salt of said compound, or (iv) an isomer of said compound, analog, or salt, wherein, for Formula XI, R$^2$ is selected from the groups listed in Tables 9.2 and 15.1, and wherein, for Formula XII, R$^4$ is selected from the groups listed in Tables 10.2 and 22.2.

In one embodiment, the preceding composition for decreasing p97 ATPase activity and/or degradation of a p97-dependent UPS substrate is provided, further including a pharmaceutically acceptable carrier.

In one embodiment, the preceding composition for decreasing p97 ATPase activity and/or degradation of a p97-dependent UPS substrate is provided, wherein the isomer is a regeoisomer or a stereoisomer.

DETAILED DESCRIPTION

Utilizing a set of dual-reporter human cell lines and a chase protocol to quantify and distinguish p97-specific inhibitors of proteasomal degradation, compounds that directly inhibit p97 and inhibit the degradation of a UPS substrate that depends on p97 were identified and characterized.

Compounds were identified as "inhibitors" if the compound had an IC$_{50}$ of 20 µM or less (potency). Inhibition was measured using a p97 ATPase assay and a p97-dependent Ub$^{G76V}$-GFP assay that measures Ub$^{G76V}$-GFP turn over. In one embodiment, a compound of the present invention decreases p97 activity and/or p97-dependent Ub$^{G76V}$-GFP-degradation turn-over to 20 µM or less. In another embodiment, the compound decreases the p97 ATPase activity and/or p97-dependent Ub$^{G76V}$-GFPdegradation turn-over to 15 µM or less. In another embodiment, the compound decreases the p97 ATPase activity and/or p97-dependent Ub$^{G76V}$-GFP degradation turn-over to 10 µM or less. In a preferred embodiment, the compound decreases the p97 ATPase activity and/or p97-dependent Ub$^{G76V}$-GFP degradation turn-over is decreased to 5 µM or less. In a most preferred embodiment, the compound decreases the p97 ATPase activity and/or p97-dependent Ub$^{G76V}$-GFP degradation turn-over to 2 µM or less.

Compounds were categorized into three types of inhibitors: 1) inhibitors of both p97 and Ub$^{G76V}$-GFP turn-over (degradation); 2) inhibitors of p97 that do not inhibit Ub$^{G76V}$-GFP turn over; and 3) inhibitors of Ub$^{G76V}$-GFP turn-over that do not inhibit p97. Comparative Examples are shown in Tables 28-33, listing compounds assayed that did not decrease either p97 or Ub$^{G76V}$-GFP turnover to at least 20 µM.

In one embodiment, a method for decreasing p97 ATPase activity and/or decreasing the degradation of the p97-dependent UPS substrate (Ub$^{G76V}$-GFP), is carried out using a compound represented by one of Formulas I-XLIII and, where applicable, having variable groups as shown in Tables 1-26.

As shown in the tables throughout, compounds and variable groups are characterized using abbreviations, which are defined as follows. In the * column of the tables, "P" refers to a purchased compound and "S" refers to a synthesized compound. R groups include H (hydrogen), C (carbon) N (nitrogen) Cl (chlorine), F (flourine), Br (bromine), NO$_2$ (nitro), Me (methyl), OMe (methoxy), Ph (phenyl), PhOMe (methoxyphenyl). Standard IUPAC nomenclature is followed for all chemical abbreviations unless indicated otherwise. Numbers preceding the atom groups indicate the position for that atom. Specific compound data is found in the enclosed NMR data (Example 9, Appendix).

Inhibitors of p97 and p97-Dependent UPS Substrate (Ub$^{G76V}$-GFP)

Tables 1-11 show compounds represented by Formulas I-XIX having an IC$_{50}$ of 20 µM or less in both a p97 ATPase assay (Example 7) and a p97-dependent Ub$^{G76V}$-GFP degradation turn-over assay (Example 8).

Formula I

TABLE 1

FORMULA I:

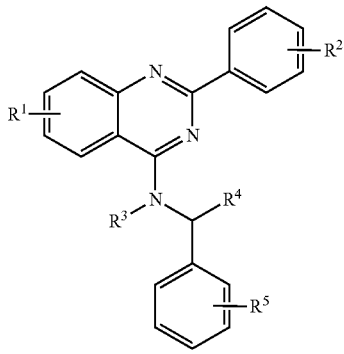

| Cpd | CID | SID | KU SCC # | * | R1 | R2 | R3 | R4 | R5 | IC$_{50}$ (μM) ATPase | Ub$^{G76V}$-GFP turn over |
|---|---|---|---|---|---|---|---|---|---|---|---|
| I-1 | 886813 | 87796231 | KSC-1-150 | P | H | 2-F | H | H | H | 3 ± 0.8 | 9.0 ± 1.3 |
| I-1 | 886813 | 96022089 | KSC-16-88 | S | H | 2-F | H | H | H | 1.1 ± 0.3 | 8 ± 1.7 |
| I-2 | 780643 | 87796227 | KSC-1-145 | P | H | H | H | H | H | 4.2 ± 2.3 | 12 ± 3 |
| I-3 | 1894007 | 87796228 | KSC-1-146 | P | H | 2-Cl | H | H | H | 1.2 ± 0.6 | 8 ± 3 |
| I-4 | 2927831 | 87796230 | KSC-1-149 | P | H | 3-NO$_2$ | H | H | H | 5.9 ± 3 | 4.0 ± 1.6 |
| I-5 | 4084712 | 87796265 | KSC-1-226 | P | H | 3-Me | H | H | H | 4.2 ± 0.2 | 17 ± 4 |
| I-6 | 1591117 | 87796273 | KSC-1-236 | P | H | 4-Cl | H | H | H | 5.5 ± 1.9 | 20 ± 3 |
| I-8 | 1187251 | 87796271 | KSC-1-234 | P | H | 4-NO$_2$ | H | H | H | 11 ± 6 | 19 ± 7 |
| I-9 | 949742 | 87796266 | KSC-1-227 | P | H | 4-OMe | H | H | H | 1.6 ± 0.3 | 15 ± 2 |
| I-10 | 3395671 | 87796263 | KSC-1-224 | P | H | 4-Me | H | H | H | 5.7 ± 0.7 | 13 ± 2 |
| I-13 | 2452802 | 87796251 | KSC-1-212 | P | H | H | H | H | 4-F | 11 ± 3 | 19 ± 3 |
| I-17 | 20963125 | 87796258 | KSC-1-219 | P | H | 4-OMe | H | H | 4-F | 7.8 ± 0.4 | 9.8 ± 3 |
| I-20 | 20963158 | 87796259 | KSC-1-220 | P | H | 4-OMe | H | H | 4-OMe | 13 ± 4 | 15 ± 5 |
| I-21 | 20963177 | 87796260 | KSC-1-221 | P | H | 4-OMe | H | H | 4-Me | 8 ± 2 | 12 ± 2 |
| I-22 | 20963187 | 87796261 | KSC-1-222 | P | H | 4-OMe | H | H | 4-Cl | 8 ± 2 | 9.3 ± 1 |
| I-23 | 20963255 | 87796262 | KSC-1-223 | P | H | 4-Cl | H | H | 4-F | 8 ± 0.2 | 20 ± 5 |
| I-24 | 4084711 | 87796264 | KSC-1-225 | P | H | 3-Me | H | H | 4-F | 15 ± 2 | 12 ± 0.8 |
| I-30 | 2790952 | 87796274 | KSC-1-237 | P | H | 4-Me | H | Me | H | 7 ± 4 | 17 ± 4 |

Formula II

TABLE 2

FORMULA II:

[Structure: quinazoline with 2-NH-phenyl-R¹ and 4-NH-benzyl substituents]

| Cpd # | CID | SID | KU SCC # | * | R1 | IC$_{50}$ (µM) ATPase | IC$_{50}$ (µM) Ub$^{G76V}$-GFP turn over |
|---|---|---|---|---|---|---|---|
| II-1 | 2909934 | 87796234 | KSC-1-153 | P | H | 2.3 ± 1 | 3.1 ± 0.4 |
| II-2 | 929548 | 87796285 | KSC-1-251 | P | 4-Me | 2.2 ± 0.4 | 6.3 ± 1.4 |
| II-3 | 2351737 | 87796281 | KSC-1-246 | P | 4-Cl | 5.4 ± 2 | 5.9 ± 1.2 |
| II-4 | 797650 | 87796284 | KSC-1-249 | P | 4-F | 3.8 ± 1.2 | 9.4 ± 1 |
| II-5 | 1943389 | 87796280 | KSC-1-245 | P | 4-Br | 1.8 ± 0.4 | 6.0 ± 0.8 |
| II-6 | 1330474 | 92093141 | KSC-1-250 | P | 4-OMe | 3.8 ± 0.5 | 4.5 ± 1.1 |
| II-6 | 1330474 | 92252642 | KSC-1-290 | S | 4-OMe | 3.5 ± 0.5 | 4.8 ± 0.7 |
| II-7 | 949445 | 87796286 | KSC-1-252 | P | 2-Me | 3.4 ± 1.5 | 10 ± 2 |
| II-9 | 886196 | 87796282 | KSC-1-247 | P | 2-F | 0.85 ± 0.17 | 10 ± 2 |
| II-11 | 1415819 | 87796283 | KSC-1-248 | P | 2-OMe | 2.2 ± 0.9 | 11 ± 3 |
| II-12 | 950033 | 87796287 | KSC-1-253 | P | 3-Me | 1.7 ± 0.5 | 3.0 ± 0.7 |
| II-13 | 1633082 | 87796279 | KSC-1-244 | P | 3-Cl | 0.48 ± 0.16 | 7.8 ± 1.3 |
| II-14 | 11645888 | 92252644 | KSC-1-292 | S | 3-F | 1.6 ± 0.1 | 2.7 ± 0.4 |
| II-15 | 45108365 | 92252645 | KSC-1-293 | S | 3-Br | 2.5 ± 0.5 | 4.3 ± 0.8 |
| II-16 | 39861404 | 92252643 | KSC-1-291 | S | 3-OMe | 2.5 ± 0.2 | 4.3 ± 0.7 |
| II-17 | 1571079 | 87796290 | KSC-1-259 | P | 3,4-di-Cl | 8.1 ± 2.6 | 12 ± 2 |
| II-18 | 45108364 | 92252647 | KSC-1-295 | S | 3-Cl-6-F | 13 ± 3 | 13 ± 2 |
| II-19 | 45108364 | 92252647 | KSC-1-294 | S | 3,5-di-Cl | 8.2 ± 0.3 | 13 ± 1 |
| II-22 | 46850871 | 99239933 | KSC-16-155 | S | 3-NO$_2$ | 5.2 ± 0.5 | 19 ± 2 |

Formula III

TABLE 3

FORMULA III:

[Structure: quinazoline with 2-NH-(3-chlorophenyl) and 4-NH-benzyl-R¹ substituents]

| Cpd # | CID | SID | KU SCC # | * | R1 | IC$_{50}$ (µM) ATPase | IC$_{50}$ (µM) Ub$^{G76V}$-GFP turn over |
|---|---|---|---|---|---|---|---|
| III-1 | 46173070 | 96022083 | KSC-16-72 | S | 4-Me | 1.4 ± 0.3 | 12 ± 2 |
| III-2 | 46173066 | 96022090 | KSC-16-89 | S | 4-Cl | 2.8 ± 0.9 | 7.6 ± 2.4 |
| III-3 | 46173057 | 96022093 | KSC-16-98 | S | 4-F | 1.5 ± 0.3 | 5.7 ± 1.3 |
| III-4 | 46173059 | 96022096 | KSC-16-101 | S | 4-Br | 7.4 ± 2 | 10 ± 3 |
| III-5 | 46173063 | 96022086 | KSC-16-79 | S | 4-OMe | 2.3 ± 0.6 | 11 ± 4 |
| III-6 | 46173069 | 96022080 | KSC-16-63 | S | 2-Me | 4.2 ± 1.1 | 11 ± 3 |
| III-7 | 46173062 | 96022087 | KSC-16-84 | S | 2-Cl | 4.7 ± 1.4 | 18 ± 5 |
| III-8 | 46173072 | 96022091 | KSC-16-92 | S | 2-F | 1.8 ± 0.5 | 7.8 ± 2.1 |
| III-9 | 46173058 | 96022094 | KSC-16-99 | S | 2-Br | 4 ± 1.7 | 12 ± 5 |
| III-10 | 46173067 | 96022084 | KSC-16-75 | S | 2-OMe | 1.6 ± 0.4 | 11 ± 2 |
| III-11 | 46173061 | 96022081 | KSC-16-66 | S | 3-Me | 2.3 ± 0.6 | 9.7 ± 2.7 |
| III-12 | 46173068 | 96022088 | KSC-16-87 | S | 3-Cl | 5 ± 1.2 | 15 ± 4 |
| III-13 | 46173060 | 96022092 | KSC-16-95 | S | 3-F | 1.2 ± 0.2 | 6.3 ± 1.7 |
| III-14 | 46173065 | 96022095 | KSC-16-100 | S | 3-Br | 3.7 ± 0.9 | 9.9 ± 2 |
| III-15 | 46173071 | 96022085 | KSC-16-78 | S | 3-OMe | 1 ± 0.1 | 9.9 ± 1.6 |

Formula IV

TABLE 4

FORMULA IV:

| Cpd | CID | SID | KU SCC # | * | R1 | IC$_{50}$ (μM) ATPase | Ub$^{G76V}$-GFP turn over |
|---|---|---|---|---|---|---|---|
| IV-1 | 25144450 | 93374186 | KSC-1-300 | S | 4-Me | 3 ± 0.3 | 1.5 ± 0.4 |
| IV-2 | 45382112 | 93374224 | KSC-16-33 | S | 4-Cl | 3.1 ± 0.2 | 2.1 ± 0.4 |
| IV-3 | 45382121 | 93374227 | KSC-16-38 | S | 4-F | 2.6 ± 0.2 | 3.4 ± 0.5 |
| IV-4 | 45382119 | 93374230 | KSC-16-42 | S | 4-Br | 4.3 ± 0.9 | 3.9 ± 0.3 |
| IV-5 | 45382111 | 93374187 | KSC-16-2 | S | 4-OMe | 3 ± 0.5 | 1.3 ± 0.2 |
| IV-6 | 45382120 | 93374191 | KSC-16-8 | S | 2-Me | 2.7 ± 0.5 | 1.9 ± 0.4 |
| IV-7 | 45382117 | 93374222 | KSC-16-31 | S | 2-Cl | 5.3 ± 1.2 | 2.9 ± 0.9 |
| IV-8 | 45382108 | 93374225 | KSC-16-35 | S | 2-F | 2.9 ± 0.4 | 2.8 ± 0.4 |
| IV-9 | 45382107 | 93374228 | KSC-16-40 | S | 2-Br | 2.0 ± 0.3 | 3.8 ± 0.7 |
| IV-10 | 45382105 | 93374193 | KSC-16-29 | S | 2-OMe | 3.6 ± 0.8 | 1.9 ± 0.2 |
| IV-11 | 45382113 | 93374192 | KSC-16-28 | S | 3-Me | 2.3 ± 0.4 | 2.5 ± 0.5 |
| IV-12 | 45382114 | 93374223 | KSC-16-32 | S | 3-Cl | 2.7 ± 0.1 | 2.5 ± 0.4 |
| IV-13 | 45382110 | 93374226 | KSC-16-36 | S | 3-F | 3.1 ± 0.4 | 2.8 ± 0.4 |
| IV-14 | 45382118 | 93374229 | KSC-16-41 | S | 3-Br | 3.7 ± 0.4 | 2.8 ± 0.4 |
| IV-15 | 45382116 | 93374221 | KSC-16-30 | S | 3-OMe | 4.5 ± 0.8 | 2.5 ± 0.8 |
| IV-16 | 45382109 | 93374190 | KSC-16-6 | S | 4-CF$_3$ | 2.6 ± 0.4 | 2.3 ± 0.3 |
| IV-17 | 45382106 | 93374188 | KSC-16-3 | S | 3,4-di-Cl | 3 ± 0.5 | 1.9 ± 0.2 |
| IV-18 | 45382115 | 93374189 | KSC-16-4 | S | 4-Cl-3-CF$_3$ | 4.7 ± 1 | 2.2 ± 0.4 |

Formula V

TABLE 5

FORMULA V:

| Cpd | CID | SID | KU SCC # | * | R1 | IC$_{50}$ (μM) ATPase | Ub$^{G76V}$-GFP turn over |
|---|---|---|---|---|---|---|---|
| V-1 | 46224527 | 96079523 | KSC-16-103 | S | 3-Cl-2-OMe | 0.9 ± 0.2 | 6.3 ± 1.7 |
| V-2 | 46224522 | 96079524 | KSC-16-104 | S | 3-F-2-Me | 0.9 ± 0.1 | 3.7 ± 0.8 |
| V-3 | 46224524 | 96079525 | KSC-16-105 | S | 3-F-5-Me | 0.7 ± 0.05 | 5.4 ± 0.8 |
| V-4 | 46224529 | 96079526 | KSC-16-105 | S | 3-F-2-OMe | 1.7 ± 0.5 | 12 ± 3 |
| V-5 | 46224523 | 96079527 | KSC-16-107 | S | 3-Cl-2-Me | 0.7 ± 0.1 | 5.5 ± 1 |
| V-6 | 46224519 | 96079528 | KSC-16-108 | S | 3-F-6-Me | 0.8 ± 0.1 | 5 ± 1 |
| V-7 | 46224528 | 96079529 | KSC-16-109 | S | 3-F-4-Me | 0.9 ± 0.2 | 5.2 ± 1.2 |
| V-8 | 46224530 | 96079530 | KSC-16-110 | S | 3-F-4-OMe | 0.9 ± 0.1 | 4.7 ± 0.8 |
| V-9 | 46224526 | 96079531 | KSC-16-112 | S | 3-Cl-6-Me | 0.8 ± 0.07 | 7 ± 1.5 |
| V-10 | 46224518 | 96079532 | KSC-16-113 | S | 3-Cl-6-OMe | 1.1 ± 0.2 | 16 ± 6 |
| V-11 | 46829342 | 99206553 | KSC-16-120 | S | 3-F-6-OMe | 6.7 ± 3 | 9.3 ± 1 |

Formula VI

TABLE 6

FORMULA VI:

| Cpd # | CID | SID | KU SCC # | * | R1 | IC$_{50}$ (μM) ATPase | Ub$^{G76V}$-GFP turn over |
|---|---|---|---|---|---|---|---|
| VI-1 | 46224525 | 96079533 | KSC-16-114 | S | 5-Cl | 2.2 ± 0.7 | 16 ± 2 |

TABLE 6-continued

FORMULA VI:

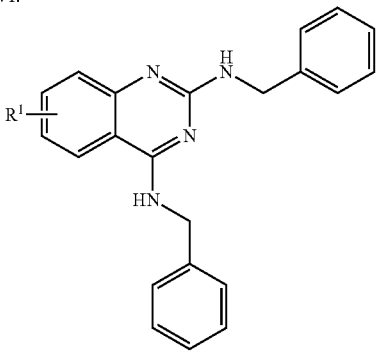

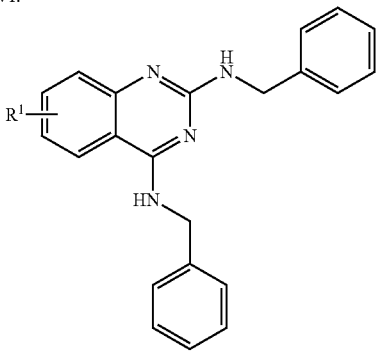

| Cpd # | CID | SID | KU SCC # | * | R1 | ATPase | Ub$^{G76V}$-GFP turn over |
|---|---|---|---|---|---|---|---|
| VI-2 | 46224521 | 96079534 | KSC-16-115 | S | 5-F | 1.2 ± 0.3 | 13 ± 2 |
| VI-3 | 46224520 | 96079535 | KSC-16-117 | S | 6-Cl | 1.6 ± 0.4 | 6.6 ± 0.9 |
| VI-4 | 5276745 | 96022097 | KSC-16-102 | S | 6,7-di-OMe | 4.4 ± 1.8 | 8.8 ± 1.5 |
| VI-5 | 46829340 | 99206522 | KSC-16-121 | S | 8-OMe | 0.6 ± 0.06 | 10 ± 2 |
| VI-6 | 46829333 | 99206552 | KSC-16-118 | S | 7-Me | 2.2 ± 0.4 | 6.1 ± 1.6 |
| VI-7 | 46850874 | 99239928 | KSC-16-160 | S | 7-CF$_3$ | 9.1 ± 2 | 19 ± 1 |
| VI-9 | 46850882 | 99239931 | KSC-16-153 | S | 8-Br | 3.3 ± 0.9 | 30 ± 2 |
| VI-10 | 46850883 | 99239932 | KSC-16-154 | S | 8-F | 3.1 ± 0.5 | 18 ± 2 |
| VI-11 | 46850884 | 99239934 | KSC-16-156 | S | 7-F | 2.6 ± 0.5 | 6.1 ± 0.8 |
| VI-12 | 46850880 | 99239935 | KSC-16-159 | S | 7-Cl | 5.5 ± 0.9 | 6.3 ± 0.9 |
| VI-13 | 46850885 | 99239938 | KSC-16-166 | S | 7-OMe | 5.7 ± 1 | 42 ± 6 |
| VI-14 | 46850877 | 99239939 | KSC-16-172 | S | 6-OMe | 7.5 ± 1.1 | 8.6 ± 1.7 |
| VI-15 | 46850873 | 99239941 | KSC-16-175 | S | 6-F | 4.7 ± 0.4 | 8.2 ± 1.5 |

Formula VII

TABLE 7

FORMULA VII:

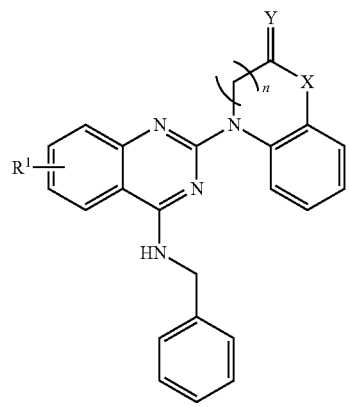

| Cpd # | CID | SID | KU SCC # | * | R1 | n | X | Y** | ATPase | Ub$^{G76V}$-GFP turn over |
|---|---|---|---|---|---|---|---|---|---|---|
| VII-1 | 46829336 | 99239922 | KSC-16-125 | S | H | 1 | CH$_2$ | H, H | 4.4 ± 1.8 | 10 ± 2 |
| VII-2 | 46829332 | 99239923 | KSC-16-144 | S | H | 0 | CH$_2$ | H, H | 2 ± 0.5 | 11 ± 3 |
| VII-3 | 46173064 | 96022082 | KSC-16-70 | S | H | 1 | O | H, H | 0.6 ± 0.2 | 7 ± 1.9 |
| VII-4 | 46829338 | 99206557 | KSC-16-147 | S | H | 1 | NH | H, H | 0.4 ± 0.05 | 6.3 ± 1 |
| VII-5 | 46873816 | 99313586 | KSC-16-182 | S | 8-OMe | 1 | NH | H, H | 0.9 ± 0.1 | 3.7 ± 0.2 |

TABLE 7-continued
FORMULA VII:
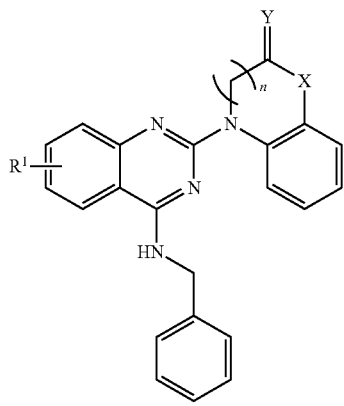
| Cpd # | CID | SID | KU SCC # | * | R1 | n | X | Y** | IC$_{50}$ (μM) ATPase | Ub$^{G76V}$-GFP turn over |
|---|---|---|---|---|---|---|---|---|---|---|
| VII-6 | 4687 3819 | 9931 3591 | KSC-16-191 | S | 8-OMe | 1 | O | H, H | 0.2 ± 0.02 | 3.3 ± 0.4 |
| VII-7 | 4693 1212 | 9943 7738 | KSC-16-232 | S | 8-OH | 1 | O | H, H | 1.2 ± 0.3 | 7.7 ± 1.7 |
| VII-8 | 4983 0264 | 1039 0418 0 | KSC-16-255 | S | 8-Ph | 1 | O | H, H | 3.5 ± 0.6 | 5 ± 0.9 |
| VII-9 | 4983 0253 | 1039 0418 1 | KSC-16-260 | S | 8-OCH$_2$CH$_2$OH | 1 | O | H, H | 0.17 ± 0.05 | 3.8 ± 0.8 |
| VII-10 | 4983 0265 | 1039 0418 3 | KSC-16-265 | S | 8OCH$_2$CH$_2$NEt$_2$ | 1 | O | H, H | 0.4 ± 0.08 | 5.3 ± 0.6 |
| VII-11 | 4983 0267 | 1039 0418 4 | KSC-16-268 | S | 8-p-OMePh | 1 | O | H, H | 1.1 ± 0.1 | 9 ± 1 |
| VII-12 | 4985 2177 | 1042 2195 2 | KSC-25-17 | S | 8-OMe | 1 | NMe | H, H | 3.1 ± 0.5 | 7.8 ± 0.7 |
| VII-13 | 4985 2173 | 1042 2195 3 | KSC-25-15c1 | S | 8-OMe | 1 | NCOMe | H, H | 2.7 ± 0.6 | 8 ± 1 |
| VII-14 | 4985 2181 | 1042 2195 7 | KSC-25-29 | S | 8-OCH$_2$CH$_2$OMe | 1 | O | H, H | 0.6 ± 0.03 | 6.5 ± 0.7 |
| VII-16 | 4983 0258 | 1039 0416 9 | KSC-16-270 | S | 8-OMe | 0 | NH | NH | 0.11 ± 0.03 | 0.9 ± 0.1 |
| VII-17 | 4983 0270 | 1039 0417 2 | KSC-16-262cc | S | 8-OMe | 0 | O | O | 0.11 ± 0.03 | 5 ± 1 |

Formulas VIII to X
TABLE 8
| Cpd | CID | SID | KU SCC # | * | IC$_{50}$ (μM) | |
|---|---|---|---|---|---|---|
| | | | | | ATPase | Ub$^{G76V}$-GFP turn over |
| VIII | 4983 0260 | 1039 0418 5 | KSC-16-290 | S | 0.11 ± 0.03 | 3.5 ± 0.4 |
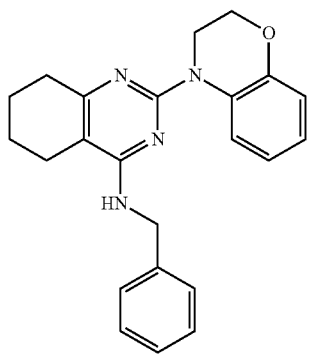 [SMILES: c1ccc(CNc2nc(N3CCOc4ccccc43)nc3c2CCCC3)cc1]
Formula VIII
| IX | 4985 2184 | 1042 2195 0 | KSC-25-14 | S | 0.4 ± 0.1 | 6.4 ± 1 |
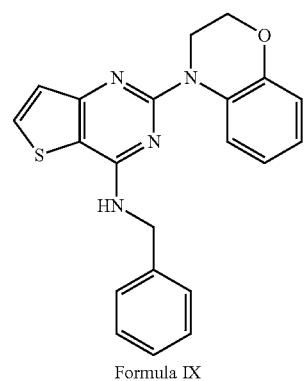
Formula IX
| X | 4985 2172 | 1042 2195 5 | KSC-25-24 | S | 1.1 ± 0.2 | 10 ± 1 |
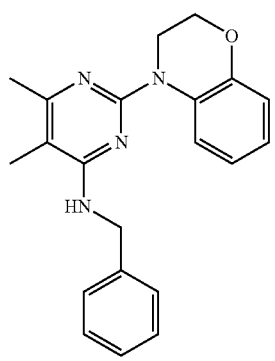 [SMILES: Cc1nc(N2CCOc3ccccc32)nc(NCc2ccccc2)c1C]
Formula X Formula XI
TABLE 9
Formula XI:
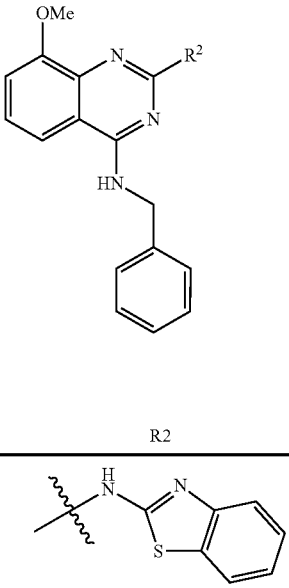
| Cpd # | CID | SID | KU SCC # | * | R2 | IC$_{50}$ (uM) ATPase | Ub$^{G76V}$-GFP turn over |
|---|---|---|---|---|---|---|---|
| XI-5 | 4985 2185 | 10422 1947 | KSC-25-22 | S | 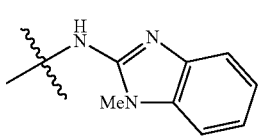 [SMILES: *Nc1nc2ccccc2n1C] | 0.5 ± 0.2 | 14 ± 2 |
| XI-6 | 4985 2183 | 10422 1949 | KSC-25-21 | S | 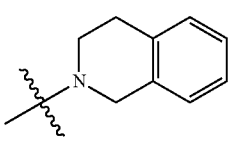 [SMILES: *N1CCc2ccccc2C1] | 0.3 ± 0.07 | 7.8 ± 1.2 |
| XI-8 | 2514 4452 | 99313 587 | KSC-16-187 | S | 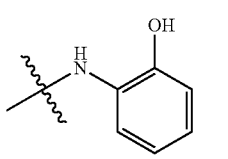 [SMILES: *Nc1ccccc1O] | 15 ± 3 | 7 ± 1.3 |
| XI-10 | 4693 1213 | 99437 735 | KSC-16-203 | S | 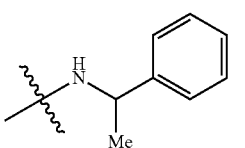 [SMILES: *NC(C)c1ccccc1] | 2.6 ± 0.4 | 2.8 ± 0.5 |
| XI-11 | 4983 0269 | 10390 4171 | KSC-16-273 | S | 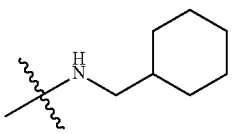 [SMILES: *NCC1CCCCC1] | 12 ± 5 | 2.1 ± 0.7 |
| XI-13 | 4983 0255 | 10390 4174 | KSC-16-278 | S | 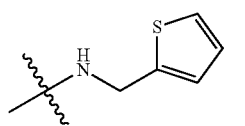 [SMILES: *NCc1cccs1] | 5.4 ± 0.9 | 4.2 ± 1 |
| XI-14 | 4983 0257 | 10390 4175 | KSC-16-282 | S | 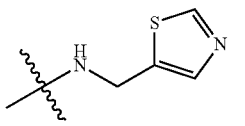 [SMILES: *NCc1cncs1] | 1.7 ± 0.4 | 1.8 ± 0.3 |
| XI-15 | 4983 0266 | 10390 4176 | KSC-16-283 | S |  | 11 ± 1 | 10 ± 3 |

TABLE 9-continued
Formula XI:
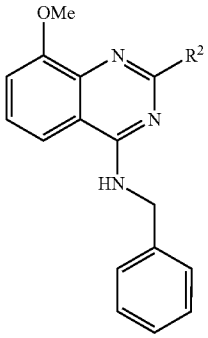
| Cpd # | CID | SID | KU SCC # | * | R2 | IC₅₀ (uM) ATPase | Ub$^{G76V}$-GFP turn over |
|---|---|---|---|---|---|---|---|
| XI-16 | 4687 3815 | 99313 592 | KSC-16-193 | S | 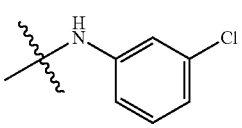 [SMILES: *Nc1cccc(Cl)c1] | 0.5 ± 0.1 | 5.4 ± 1 |
| XI-17 | 4687 3818 | 99313 593 | KSC-16-194 | S | 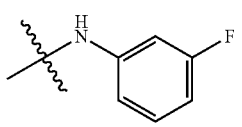 [SMILES: *Nc1cccc(F)c1] | 0.52 ± 0.04 | 4.8 ± 0.7 |
| XI-18 | 4687 3813 | 99313 594 | KSC-16-196 | S | 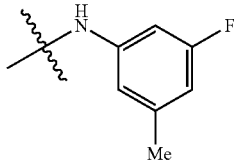 [SMILES: *Nc1cc(C)cc(F)c1] | 1.5 ± 0.2 | 7.1 ± 0.5 |
Formula XII
TABLE 10
FORMULA XII:
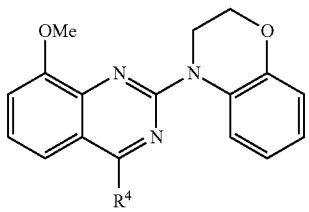
| Cpd # | CID | SID | KU SCC # | * | R4 | IC₅₀ (uM) ATPase | Ub$^{G76V}$-GFP turn over |
|---|---|---|---|---|---|---|---|
| XII-4 | 49830 256 | 10390 4182 | KSC-16-261 | S | 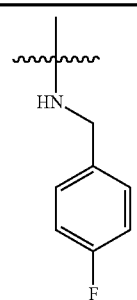 | 1.9 ± 0.4 | 3.7 ± 0.6 |

TABLE 10-continued
FORMULA XII:
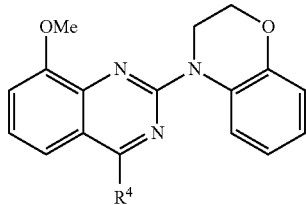
| Cpd # | CID | SID | KU SCC # | * | R4 | IC$_{50}$ (uM) ATPase | Ub$^{G76V}$-GFP turn over |
|---|---|---|---|---|---|---|---|
| XII-5 | 49830261 | 103904186 | KSC-16-295 | S | HN-CH$_2$-thiophen-2-yl | 1.2 ± 0.2 | 3 ± 0.6 |
| XII-6 | 49830262 | 103904187 | KSC-16-299 | S | HN-CH$_2$-cyclohexyl | 7.4 ± 0.9 | 8.2 ± 1 |
| XII-7 | 46931214 | 99437736 | KSC-16-219 | S | HN-CH$_2$-pyridin-2-yl | 19 ± 5 | 15 ± 4 |
| XII-8 | 46931210 | 99437737 | KSC-16-222 | S | HN-CH$_2$-(2-hydroxyphenyl) | 4.6 ± 1 | 6 ± 0.6 |
| XII-10 | 46931211 | 99437740 | KSC-16-235c2 | S | HN-CH$_2$-(4-hydroxyphenyl) | 2.4 ± 0.5 | 7.3 ± 1 |

TABLE 10-continued
FORMULA XII:
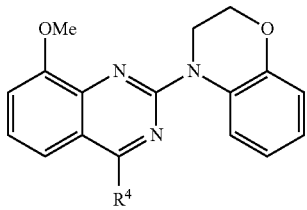
| Cpd # | CID | SID | KU SCC # | * | R4 | IC50 (uM) ATPase | Ub^{G76V}-GFP turn over |
|---|---|---|---|---|---|---|---|
Formulas XIII-XIX
TABLE 11
| Cpd # | KU SCC # | * | | IC50 (uM) ATPase | Ub^{G76V}-GFP turn over |
|---|---|---|---|---|---|
| XIII | KSC-16-13 | P | Formula XIII | 13 ± 5 | 10 ± 2 |
| XIV | KSC-16-16 | P | Formula XIV | 15 ± 5 | 14 ± 2.4 |
| XV | KSC-16-22 | P | Formula XV | 14 ± 5 | 3.7 ± 0.6 |
| XVI | KSC-16-23 | P | Formula XVI | 18 ± 8 | 5.9 ± 1 |

TABLE 11-continued

| Cpd # | KU SCC # * | | IC$_{50}$ (µM) | |
|---|---|---|---|---|
| | | | ATPase | Ub$^{G76V}$-GFP turn over |
| XVII | KSC-16-24 P | 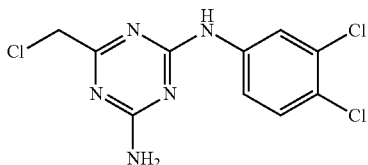 Formula XVII | 15 ± 4 | 5.7 ± 0.8 |
| XVIII | KSC-16-55 P | 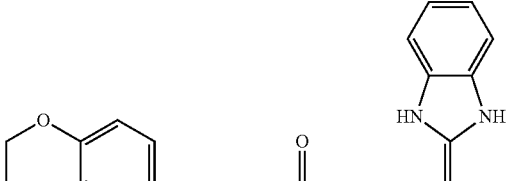 Formula XVIII | 10 ± 4 | 6.3 ± 0.6 |
| XIX | KSC-16-56 P | 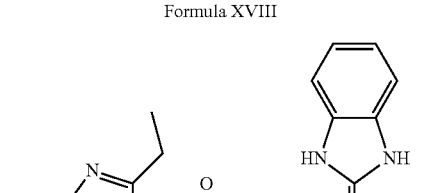 Formula XIX | 14 ± 6 | 7.2 ± 1.1 |

Inhibitors of p97

Tables 12-17 disclosed the compounds having an IC$_{50}$ of 20 µM or less in the p97 ATPase assay (Example 7), but did not decrease the p97-dependent Ub$^{G76V}$-GFP degradation turn-over assay to 20 µM or less (Example 8).

Formula I

TABLE 12

FORMULA I:

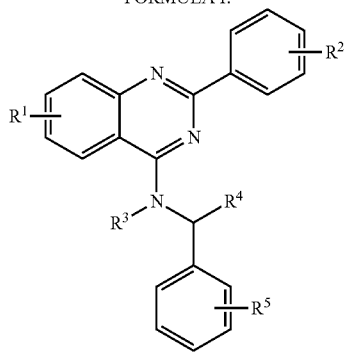

| | | | | | | | | | IC$_{50}$ (µM) | |
|---|---|---|---|---|---|---|---|---|---|---|
| Cpd # | CID | SID | KU SCC # * | R1 | R2 | R3 | R4 | R5 | ATPase | Ub$^{G76V}$-GFP turn over |
| I-11 | 18190 25 | 8779 6240 | KSC-1-200 P | H | 3,4-di-Cl | H | H | H | 7.1 ± 0.4 | 37 ± 6 |
| I-28 | 15661 44 | 8779 6272 | KSC-1-235 P | H | 4-NO$_2$ | Me | H | H | 8.4 ± 4 | 28 ± 4 |

Formula II
TABLE 13
Formula II:
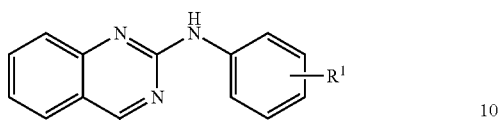
| Cpd | CID | SID | KU SCC # | * | R1 | ATPase | Ub^{G76V}-GFP turn over |
|---|---|---|---|---|---|---|---|
| II-21 | 4685 0881 | 9923 9930 | KSC-16-152 | S | 3-I | 5.2 ± 1.9 | 36 ± 4 |
IC$_{50}$ (μM)
Formula VII
TABLE 14
Formula VII:
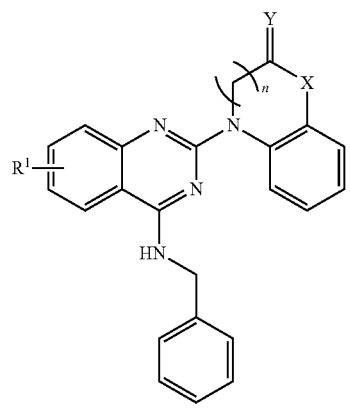
| Cpd # | CID | SID | KU SCC # | * | R1 | n | X | Y | ATPase | Ub^{G76V}-GFP turn over |
|---|---|---|---|---|---|---|---|---|---|---|
| VII-15 | 4985 2171 | 1042 2195 8 | KSC-25-30 | S | 8-nButyl | 1 | O | H, H | 2.63 ± 0.7 | 28 ± 3 |
IC$_{50}$ (μM)

Formula XI
TABLE 15
Formula XI:
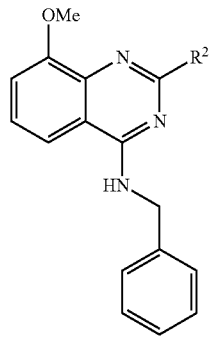
| Cpd # | CID | SID | KU SCC # | * | R2 | IC$_{50}$ (μM) ATPase | Ub$^{G76V}$-GFP turn over |
|---|---|---|---|---|---|---|---|
| XI-1 | 4985 2176 | 1042 1943 | KSC-25-3 | S | 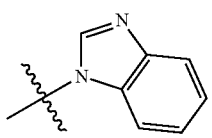 [SMILES: *n1cnc2ccccc21] | 3.3 ± 1.1 | 78 ± 45 |
| XI-12 | 4983 0259 | 1039 4173 | KSC-16-277 | S | 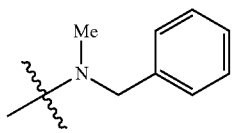 [SMILES: *N(C)Cc1ccccc1] | 7 ± 3 | >>20 |
Formula XX
TABLE 16
| Cpd # | CID | SID | KU SCC # | * | IC$_{50}$ (μM) ATPase | Ub$^{G76V}$-GFP turn over |
|---|---|---|---|---|---|---|
| XX | 4985 2180 | 10422 1956 | KSC-25-28 | S | 2.9 ± 0.2 | 27 ± 3 |
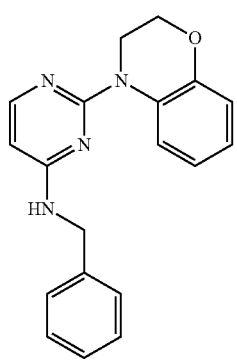 [SMILES: c1ccc(CNc2ccnc(N3CCOc4ccccc43)n2)cc1]
Formula XX Formula XXI

TABLE 17

Formula XXI

[Chemical structure: quinazoline with OMe at 8-position, 2-amino-benzimidazole at 2-position with R¹ substituent, and benzylamine (HN-CH₂-phenyl) at 4-position]

| Cpd | CID | SID | KU SCC # | * | R1 | ATPase | Ub$^{G76V}$-GFP turn over |
|---|---|---|---|---|---|---|---|
| XXI-1 | 4985 2182 | 10422 1948 | KSC-25-23 | S | 5,6-di-Me | 2 ± 0.4 | 89 ± 39 |

Inhibitors of p97-Dependent UPS Substrate Ub$^{G76V}$-GFP

Tables 18-26 disclosed the compounds having an IC$_{50}$ of 20 μM or less in the p97-dependent Ub$^{G76V}$GFP degradation turn-over assay (Example 7), but did not decrease p97 to less than 20 uM.

Formula I

TABLE 18

FORMULA I:

[Chemical structure: quinazoline with R¹ on benzene ring, 2-phenyl (with R²) at 2-position, and N(R³)-CH(R⁴)-phenyl(R⁵) at 4-position]

| Cpd | CID | SID | KU SCC # | * | R1 | R2 | R3 | R4 | R5 | ATPase | Ub$^{G76V}$-GFP turn over |
|---|---|---|---|---|---|---|---|---|---|---|---|
| I-12 | 2452792 | 87796250 | KSC-1-211 | P | H | H | H | H | 3-Cl | 28 ± 9 | 17 ± 4 |
| I-14 | 2465033 | 87796253 | KSC-1-214 | P | H | H | H | H | 2-Cl | 30 ± 10 | 11 ± 3 |
| I-15 | 2456309 | 87796254 | KSC-1-215 | P | H | H | H | H | 4-Cl | >30 | 15 ± 3 |
| I-16 | 15993188 | 87796256 | KSC-1-217 | P | H | 2-F | H | H | 2-Cl | 26 ± 12 | 15 ± 3 |
| I-25 | 1553819 | 87796289 | KSC-1-258 | P | H | H | Me | H | H | 49 ± 17 | 17 ± 5 |

TABLE 18-continued

FORMULA I:

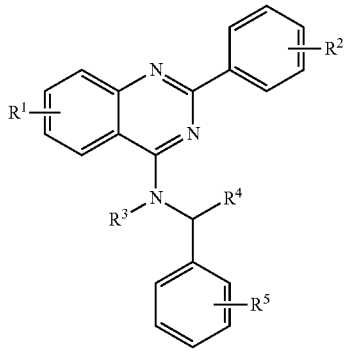

| Cpd | CID | SID | KU SCC # | * | R1 | R2 | R3 | R4 | R5 | IC₅₀ (μM) ATPase | $Ub^{G76V}$-GFP turn over |
|---|---|---|---|---|---|---|---|---|---|---|---|
| I-26 | 15995431 | 87796257 | KSC-1-218 | P | H | 2-F | Me | H | H | 25 ± 4 | 6.0 ± 2.0 |
| I-27 | 2178012 | 87796229 | KSC-1-148 | P | H | 2-NO₂ | Me | H | H | 25 ± 11 | 11 ± 6 |
| I-29 | 5051334 | 87796275 | KSC-1-238 | P | H | H | H | Me | H | 27 ± 14 | 13 ± 1 |
| I-31 | 15992808 | 87796255 | KSC-1-216 | P | H | 2-F | H | Me | H | >30 | 15 ± 4 |
| I-32 | 8074678 | 87796236 | KSC-1-193 | P | 7-Cl | H | H | H | H | 70 ± 24 | 12 ± 4 |
| I-35 | 2454628 | 87796252 | KSC-1-213 | P | H | H | CH2-* | H | 2-CH2-* | >30 | 19 ± 5 |

*$R^3$ and $R^5$ are connected

Formula II

TABLE 19

FORMULA II:

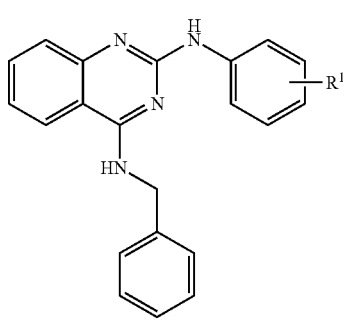

| Cpd | CID | SID | KU SCC # | * | R1 | IC₅₀ (μM) ATPase | $Ub^{G76V}$-GFP turn over |
|---|---|---|---|---|---|---|---|
| II-8 | 2384230 | 92252641 | KSC-1-289 | S | 2-Cl | 69 ± 25 | 13 ± 2 |
| II-10 | 45108363 | 92252640 | KSC-1-288 | S | 2-Br | 64 ± 24 | 13 ± 2 |

Formula VI

TABLE 20

FORMULA VI:

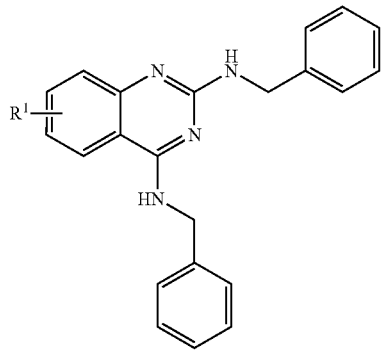

| Cpd | CID | SID | KU SCC # | * | R1 | IC₅₀ (μM) ATPase | $Ub^{G76V}$-GFP turn over |
|---|---|---|---|---|---|---|---|
| VI-16 | 46850876 | 99239943 | KSC-16-122 | S | 7-Br | 22 ± 4 | 10 ± 2 |

Formula XI
TABLE 21
Formula XI:
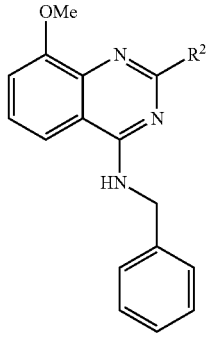
| Cpd | CID | SID | KU SCC # | * | R2 | IC$_{50}$ (μM) ATPase | Ub$^{G76V}$-GFP turn over |
|---|---|---|---|---|---|---|---|
| XI-9 | 4687 3821 | 9931 3588 | KSC-16-188 | S | 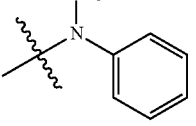 | >30 | 9.2 ± 1.2 |
Formula XII
TABLE 22
FORMULA XII:
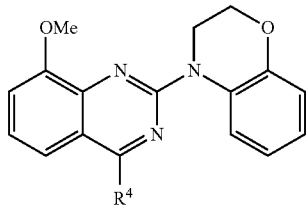
| Cpd # | CID | SID | KU SCC # | * | R4 | IC$_{50}$ (μM) ATPase | Ub$^{G76V}$-GFP turn over |
|---|---|---|---|---|---|---|---|
| XII-1 | 49852 170 | 10422 1951 | KSC-25-6 | S |  | 38 ± 7 | 20 ± 3 |
| XII-2 | 49830 271 | 10390 4178 | KSC-16-243 | S | 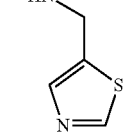 | 52 ± 10 | 19 ± 4 |

TABLE 22-continued
FORMULA XII:
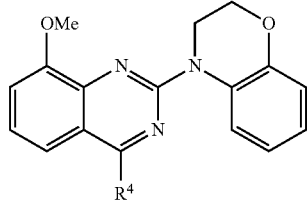
| Cpd # | CID | SID | KU SCC # | * | R4 | IC$_{50}$ (μM) ATPase | Ub$^{G76V}$-GFP turn over |
|---|---|---|---|---|---|---|---|
| XII-9 | 46931215 | 99437739 | KSC-16-227 | S | (benzyl-NMe$_2$ amine) | 47 ± 22 | 4.5 ± 0.5 |
| XII-11 | 46873814 | 99313590 | KSC-16-190 | S | (3,4-dihydro-2H-benzo[b][1,4]oxazine) | >30 | 8.1 ± 1.8 |
Formulas XXII-XXIV
TABLE 23
| Cpd | CID | SID | KU SCC # | * | | IC$_{50}$ (μM) ATPase | Ub$^{G76V}$-GFP turn over |
|---|---|---|---|---|---|---|---|
| XXII | 696840 | 87796233 | KSC-1-152 | P | Formula XXII | 26 ± 4 | 7.3 ± 2 |
| XXIII | 1337599 | 92093137 | KSC-1-203 | P | Formula XXIII | 33 ± 8 | 12 ± 1 |

TABLE 23-continued
| Cpd | CID | SID | KU SCC # | * | ATPase | IC$_{50}$ (μM) Ub$^{G76V}$-GFP turn over |
|---|---|---|---|---|---|---|
| XXIV | 4687 3817 | 9931 3595 | KSC-16-197 | S | >30 | 11 ± 0.8 |
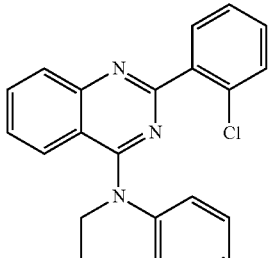
Formula XXIV
Formula XXV
TABLE 24
Formula XXV
| Cpd # | CID | SID | KU SCC # | * | R1 | R2 | ATPase | IC$_{50}$ (μM) Ub$^{G76V}$-GFP turn over |
|---|---|---|---|---|---|---|---|---|
| XXV-2 | 4685 0879 | 9923 9936 | KSC-16-163 | S | 3-Cl | H | 34 ± 16 | 12 ± 2 |
| XXV-3 | 4685 0870 | 9923 9937 | KSC-16-164 | S | 3-Cl | 4-OMe | 34 ± 14 | 13 ± 1 |
Formula XXVI-XLI
TABLE 25
| Cpd # | KU SCC # | * | ATPase | IC$_{50}$ (μM) Ub$^{G76V}$-GFP turn over |
|---|---|---|---|---|
| XXVI | KSC-16-16 | P | ND (no data) | 10.4 ± 1.5 |
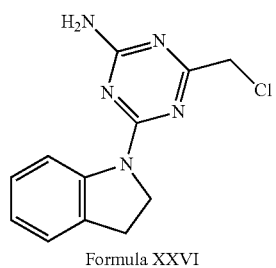
Formula XXVI TABLE 25-continued
| Cpd # | KU SCC # | * | | IC$_{50}$ (μM) | |
|---|---|---|---|---|---|
| | | | | ATPase | Ub$^{G76V}$-GFP turn over |
| XXVII | KSC-16-22 | P | 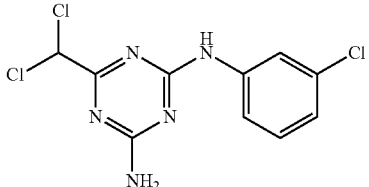 Formula XXVII | ND | 13 ± 3 |
| XXVIII | KSC-16-11 | P | 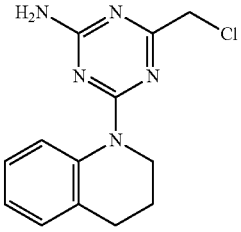 [SMILES: Nc1nc(CCl)nc(N2CCCc3ccccc32)n1] Formula XXVIII | ND | 17 ± 3 |
| XXIX | KSC-16-14 | P | 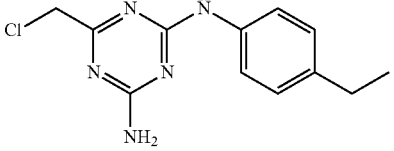 Formula XXIX | ND | 18 ± 3 |
| XXX | KSC-16-18 | P | 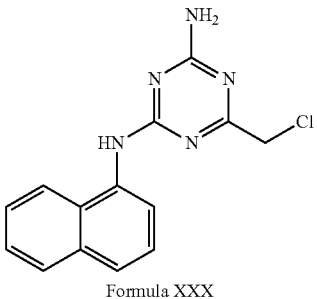 Formula XXX | ND | 14 ± 3 |
| XXXI | KSC-16-45 | P | 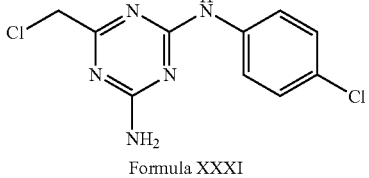 Formula XXXI | ND | 8 ± 2 |
| XXXII | KSC-16-46 | P | 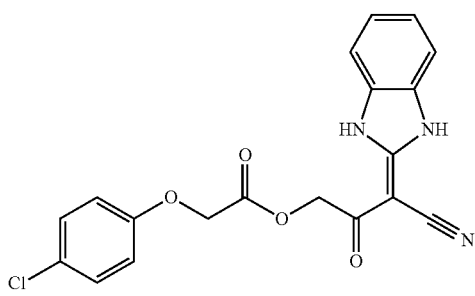 [SMILES: N#CC(C(=O)COC(=O)COc1ccc(Cl)cc1)=C1Nc2ccccc2N1] Formula XXXII | ND | 2.6 ± 0.2 |

TABLE 25-continued

| Cpd # | KU SCC # | * | Structure | IC$_{50}$ (μM) ATPase | Ub$^{G76V}$-GFP turn over |
|---|---|---|---|---|---|
| XXXIII | KSC-16-47 | P | Formula XXXIII | ND | 3.4 ± 0.6 |
| XXXIV | KSC-16-48 | P | Formula XXXIV | ND | 5.9 ± 0.8 |
| XXXV | KSC-16-49 | P | Formula XXXV | ND | 6.1 ± 0.6 |
| XXXVI | KSC-16-50 | P | Formula XXXVI | ND | 15 ± 2 |

TABLE 25-continued
| Cpd # | KU SCC # | * | | IC$_{50}$ (μM) | |
|---|---|---|---|---|---|
| | | | | ATPase | Ub$^{G76V}$-GFP turn over |
| XXXVII | KSC-16-51 | P | 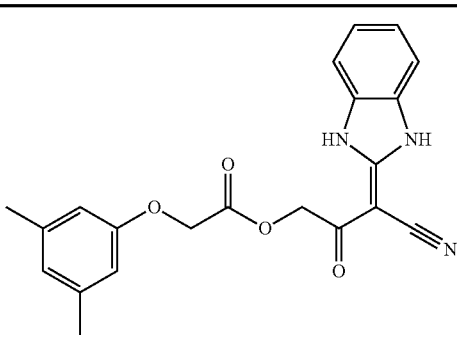 Formula XXXVII | ND | 13 ± 1.4 |
| XXXVIII | KSC-16-53 | P | 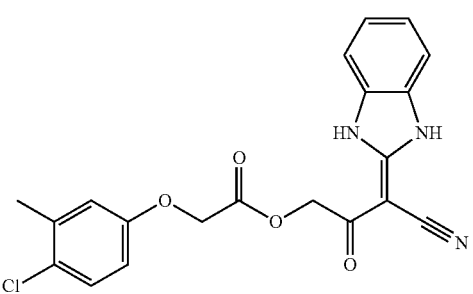 [SMILES: Cc1cc(OCC(=O)OCC(=O)C(C#N)=C2Nc3ccccc3N2)ccc1Cl] Formula XXXVIII | ND | 16 ± 1.4 |
| XXXIX | KSC-16-55 | P | 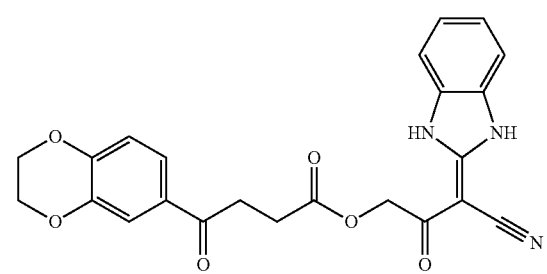 [SMILES: N#CC(C(=O)COC(=O)CCC(=O)c1ccc2c(c1)OCCO2)=C1Nc2ccccc2N1] Formula XXXIX | ND | 6.3 ± 0.6 |
| XL | KSC-16-57 | P | 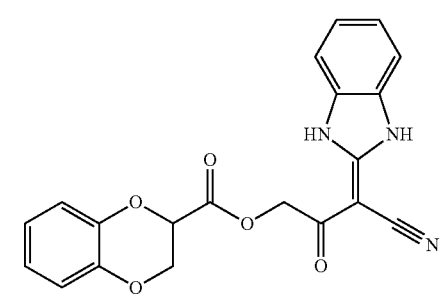 [SMILES: N#CC(C(=O)COC(=O)C1COc2ccccc2O1)=C1Nc2ccccc2N1] Formula XL | ND | 10 ± 1.4 |

TABLE 25-continued

| Cpd # | KU SCC # | * | IC$_{50}$ (μM) ATPase | Ub$^{G76V}$-GFP turn over |
|---|---|---|---|---|
| XLI | KSC-16-59 | P | ND | 6.5 ± 0.8 |

Formula XLI

Formulas XLII and XLIII

TABLE 26

| Cpd # | CID | SID | KU SCC # | * | IC$_{50}$ (μM) ATPase | Ub$^{G76V}$-GFP turn over |
|---|---|---|---|---|---|---|
| XLII | 46873820 | 99313589 | KSC-16-189 | S | >30 | 11 ± 2 |

Formula XLII

| XLIII | 49830263 | 103904177 | KSC-16-241 | S | 30 ± 6 | 16 ± 2 |

Formula XLIII

COMPARATIVE EXAMPLES

In the following Tables 27-33, compounds are shown that did not decrease either p97 or Ub$^{G76V}$-GFP to 20 μM or less.

Formula I

TABLE 27

Formula I:

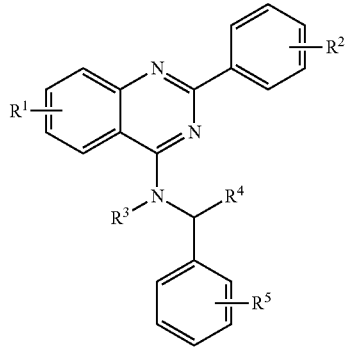

| | | | | | | | | | | IC$_{50}$ (μM) | |
|---|---|---|---|---|---|---|---|---|---|---|---|
| Cpd # | CID | SID | KU SCC # | * | R1 | R2 | R3 | R4 | R5 | ATPase | Ub$^{G76V}$-GFP turn over |
| I-7 | 2047240 | 87796235 | KSC-1-147 | P | H | 4-Br | H | H | H | 72 ± 14 | 25 ± 10 |
| I-33 | 8080035 | 87796237 | KSC-1-194 | P | 7-Cl | 4-Me | H | H | H | 39 ± 13 | 24 ± 5 |
| I-34 | 8080040 | 87796238 | KSC-1-195 | P | 7-Cl | 4-OMe | H | H | H | 25 ± 11 | 70 ± 30 |

Formula II

TABLE 28

FORMULA II:

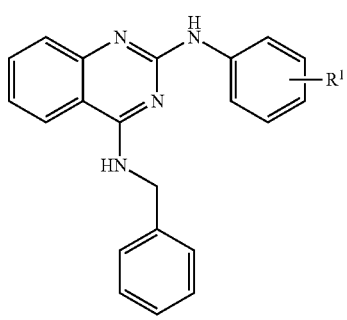

| | | | | | | IC$_{50}$ (μM) | |
|---|---|---|---|---|---|---|---|
| Cpd # | CID | SID | KU SSC # | * | R1 | ATPase | Ub$^{G76V}$-GFP turn over |
| II-20 | 46829335 | 99239925 | KSC-16-150 | S | 3-CF3 | 50 ± 16 | 21 ± 1 |

Formula VI

TABLE 29

FORMULA VI:

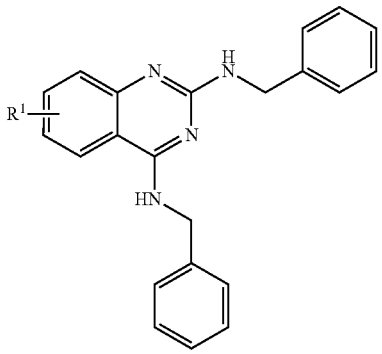

| | | | | | | IC$_{50}$ (μM) | |
|---|---|---|---|---|---|---|---|
| Cpd # | CID | SID | KU SCC # | * | R1 | ATPase | Ub$^{G76V}$-GFP turn over |
| VI-8 | 46850869 | 99239929 | KSC-16-167 | S | 7-CN | 25 ± 10 | 21 ± 3 |

Formula XI
TABLE 30
Formula XI:
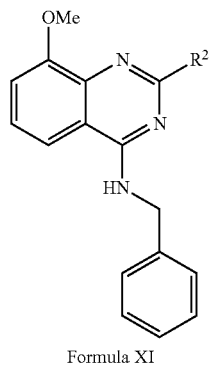
Formula XI
| Cpd # | CID | SID | KU SCC # | * | R2 | IC$_{50}$ (μM) ATPase | Ub$^{G76V}$-GFP turn over |
|---|---|---|---|---|---|---|---|
| XI-2 | 49852179 | 10422194 | KSC-25-10 | S | morpholine | 31 ± 7 | 47 ± 9 |
| XI-3 | 49852174 | 10422195 | KSC-25-12 | S | –NH–C(O)–NH$_2$ | 49 ± 10 | 108 ± 31 |
| XI-4 | 49852178 | 10422196 | KSC-25-16 | S | 4-methylpiperazine | >>30 | 45 ± 18 |
| XI-7 | 49852175 | 10422195 4 | KSC-25-17 | S | –NH–C(O)–N(CH$_3$)$_2$ | 60 ± 23 | 37 ± 7 |
| XI-19 | 49830268 | 10390417 0 | KSC-16-272 | S | 4-acetylpiperazine | >30 | >>20 |

Formula XII
TABLE 31
FORMULA XII:
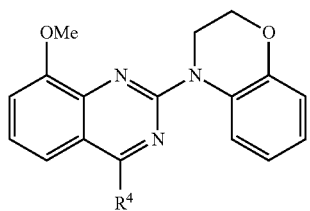
| Cpd # | CID | SID | KU SCC # | * | R4 | IC$_{50}$ ($\mu$M) ATPase | Ub$^{G76V}$-GFP turn over |
|---|---|---|---|---|---|---|---|
| XII-3 | 4983 0254 | 10390 4179 | KSC-16-251 | S | | 33 ± 7 | 23 ± 2 |
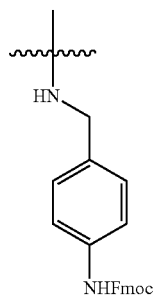
Formula XXV
TABLE 32
Formula XXV
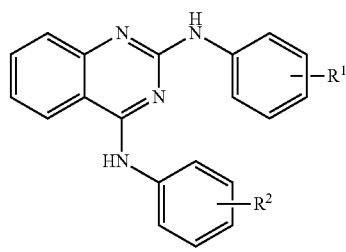
| Cpd # | CID | SID | KU SCC # | * | R1 | R2 | IC$_{50}$ ($\mu$M) ATPase | Ub$^{G76V}$-GFP turn over |
|---|---|---|---|---|---|---|---|---|
| XXV-1 | 1732 4423 | 9923 9924 | KSC-16- 149 | S | 4-OMe | 4-OMe | 22 ± 4 | 23 ± 3 |
| XXV-4 | 4685 0872 | 9923 9940 | KSC-16- 174 | S | 3-Cl | 4-Me | 49 ± 19 | 30 ± 4 |
| XXV-5 | 4685 0878 | 9923 9942 | KSC-16- 176 | S | 3-Cl | 4-Cl | 117 ± 5.8 | 21 ± 2 |
| XXV-6 | 4685 0875 | 9923 9944 | KSC-16- 151 | S | 4-Me | 4-Me | 54 ± 19 | 21 ± 4 |

Formulas XLIV-XLXI

TABLE 33

| Cpd # | CID | SID | KU SCC # | * | | IC$_{50}$ (µM) | |
|---|---|---|---|---|---|---|---|
| | | | | | | ATPase | Ub$^{G76V}$-GFP turn over |
| XLIV | 832282 | 87796232 | KSC-1-151 | P | Formula XLIV | 23 ± 6 | 36 ± 9 |
| XLV | 832283 | 92093143 | KSC-1-260 | P | Formula XLV | 53 ± 18 | 31 ± 6 |
| XLVI | 2950240 | 87796276 | KSC-1-240 | P | Formula XLVI | 34 ± 10 | 36 ± 0.3 |
| XLVII | 1330669 | 87796248 | KSC-1-208 | P | Formula XLVII | 34 ± 11 | 35 ± 5 |

TABLE 33-continued

| Cpd # | CID | SID | KU SCC # | * | IC$_{50}$ (μM) ATPase | Ub$^{G76V}$-GFP turn over |
|---|---|---|---|---|---|---|
| XLVIII | 2955641 | 87796277 | KSC-1-241 | P | 22 ± 12 | 39 ± 18 |
| XLIX | 3419814 | 92093139 | KSC-1-239 | P | 43 ± 13 | 70 ± 16 |
| LI | 1091839 | 92093140 | KSC-1-242 | P | 57 ± 15 | 56 ± 10 |

Formula XLVIII

Formula XLIX

Formula L

TABLE 33-continued

| | | | | | IC$_{50}$ (μM) | |
| | | | | | ATPase | Ub$^{G76V}$-GFP turn over |
| Cpd # | CID | SID | KU SCC # | * | | |
|---|---|---|---|---|---|---|
| LI | 2932797 | 9209314 2 | KSC-1-254 | P | 30 ± 6 | 34 ± 6 |

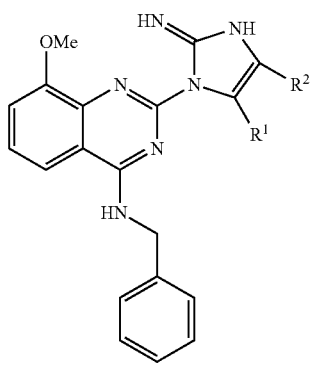

Formula LI

Compound Derivatives

In one embodiment, a compound of the present invention is a derivative of one of the compounds disclosed herein. In another embodiment of the present invention, an inhibitor of p97 ATPase is identified by assaying any of the compound derivatives of Formulas LII through LXVI in the ATPase assay as described in Example 7.

For example, a compound derivative is represented by Formula LII:

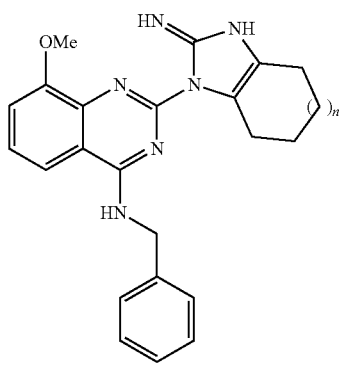

Formula LII n = 0, 1, 2

For Formula LII above, n is 0, 1 or 2. A compound of Formula LII can be synthesized as detailed in Example 3.

In another example, a compound derivative is represented by Formula LIII:

Formula LIII

For Formula LIII above, R$^1$ and R$^2$ can vary independently. R$^1$ and R$^2$ are independently selected from hydrogen (H), methyl, ethyl, propyl, or butyl. A compound of Formula LIII can be synthesized as detailed in Example 3.

In another example, a compound derivative is represented by Formula LIV:

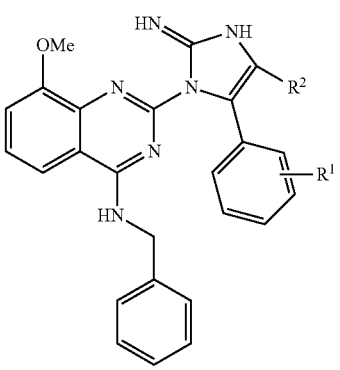

Formula LIV

For Formula LIV above, $R^1$ is selected from H, methyl, F, Cl, Br, and OMe on any position in the ring. $R^2$ is selected from hydrogen (H), methyl, ethyl, propyl and butyl. A compound of Formula LIV can be synthesized as detailed in Example 3.

In another example, a compound derivative is represented by Formula LV:

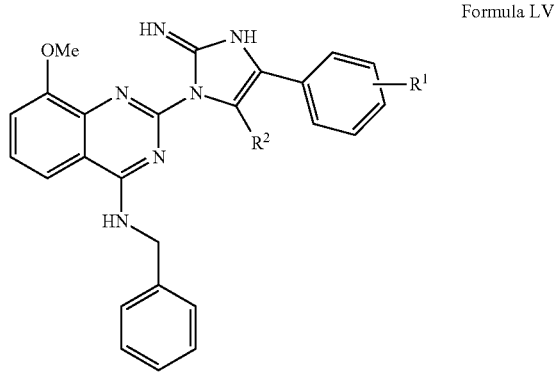

Formula LV

For Formula LV above, $R^1$ is selected from H, methyl, F, Cl, Br, and OMe on any position in the ring. A compound of Formula LV can be synthesized as detailed in Example 3.

In another example, a compound derivative is represented by Formula LVI:

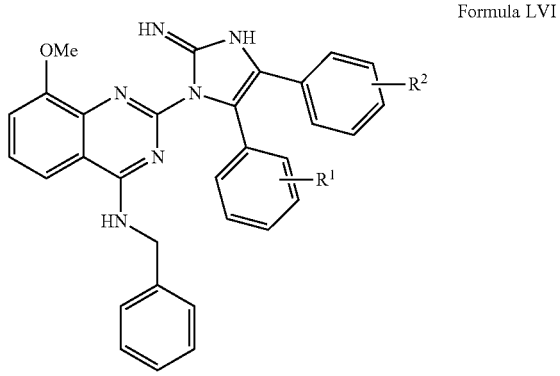

Formula LVI

For Formula LVI above, $R^1$ and $R^2$ vary independently. $R^1$ and $R^2$ are selected from H, methyl, F, Cl, Br, and OMe on any position in the ring. A compound of Formula LVI can be synthesized as detailed in Example 3.

In another example, a compound derivative is represented by Formula LVII:

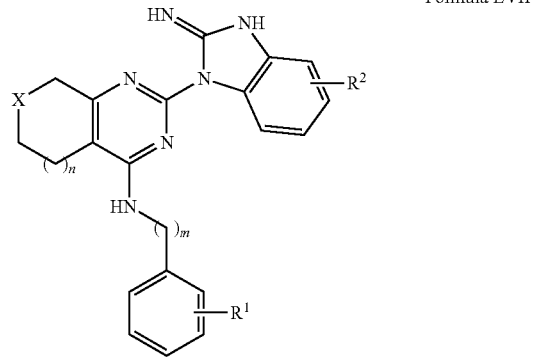

Formula LVII

For Formula LVII above, X is selected from O, NMe (nitrogen-methyl), NEt (nitrogen-ethyl), and NPh (nitrogen-phenyl) at any position in the ring; n is −1, 0, 1, or 2; and m is 1, 2, 3, or 4. $R^1$ and $R^2$ can vary independently. $R^1$ and $R^2$ are independently selected from H, Me, F, Cl, Br, and OMe at any position on the ring. A compound of Formula LVII can be synthesized as detailed in Example 4.

In another example, a compound derivative is represented by Formula LVIII:

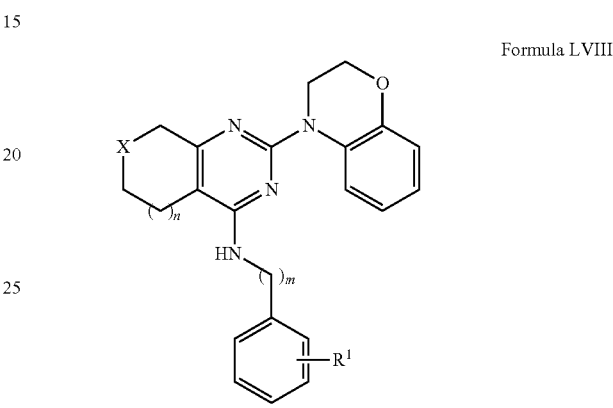

Formula LVIII

For Formula LVIII above, X is selected from O, NMe (nitrogen-methyl), NEt (nitrogen-ethyl), and NPh (nitrogen-phenyl) at any position in the ring; n is −1, 0, 1, or 2; and m is 1, 2, 3, or 4. $R^1$ is selected from H, Me, F, Cl, Br, and OMe on any position on the ring. A compound of Formula LVIII can be synthesized as detailed in Example 4.

In another example, a compound derivative is represented by Formula LIX:

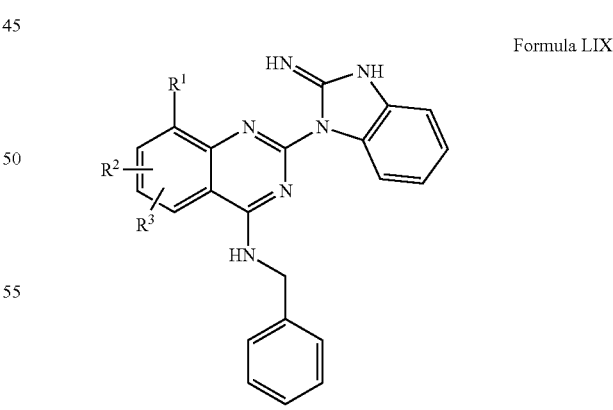

Formula LIX

For Formula LIX above, $R^1$, $R^2$ and $R^3$ can vary independently and are each independently selected from H, $A(CH_2)_nCH_3$, and $A(CH_2)_nX$, where n is 0, 1, 2, 3, 4 or 5, A=O, S or NH and X is heteroaryl, O(alkyl), S(alkyl), $(O\text{-alkyl})_2$, or $(S\text{-alkyl})_2$. A compound of Formula LIX can be synthesized as detailed in Example 5.

In another example, a compound derivative is represented by Formula LX:

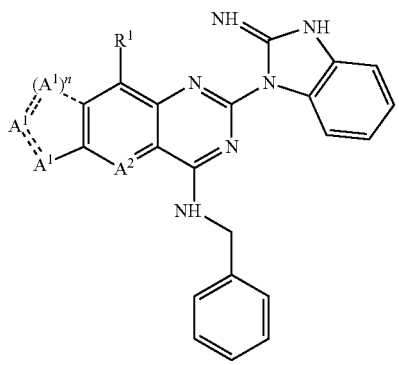

Formula LX

For Formula LX above, $R^1$ is selected from H, $A(CH_2)_nCH_3$, and $A(CH_2)_nX$, wherein n is 0, 1, 2, 3, 4, or 5, A is O, S or NH and X is selected from heteroaryl, O(alkyl), S(alkyl), (O-alkyl)$_2$, and (S-alkyl)$_2$. $A^1$ is selected from O, S, Se, N, NH, CH, $CH_2$, CHalkyl, and Calkyl; and $A^2$ is selected from N, NH, CH, and Calkyl. A compound of Formula LVX can be synthesized as detailed in Example 5.

In another example, a compound derivative is represented by Formula LXI:

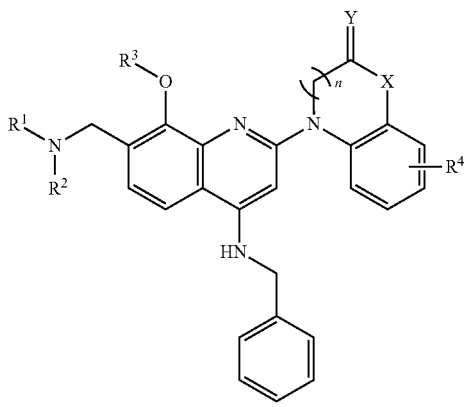

Formula LXI

X = CH2, O, NH, NMe, NEt, NCOMe, NPh
Y = NH, O, S, [H,H]
n = 0, 1

For Formula LXI above, $R^1$, $R^2$ and $R^3$ can vary independently. $R^1$, $R^2$ and $R^3$ are independently selected from alkyl, alkoxyalkyl, and aminoalkyl. $R^4$ is selected from H, halogen, alkyl, and alkyoxy. X is selected from $CH_2$, O NH, NMe, NEt, NCOMe, and NPh. Y is selected from NH, O, S, [H, H], and n is 0 or 1. A compound of Formula LXI can be synthesized as detailed in Example 6.

In another example, a compound derivative is represented by Formula LXII:

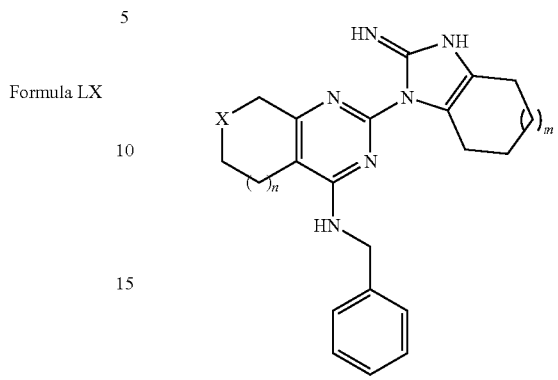

Formula LXII

For Formula LXII above, n is −1, 0, 1, or 2; m is 0, 1, or 2, and X is selected from $CH_2$, O, NMe, NEt, and NPh at any position in the ring. A compound of Formula LXII can be synthesized following a scheme as shown in Example 4.

In another example, a compound derivative is represented by Formula LXIII:

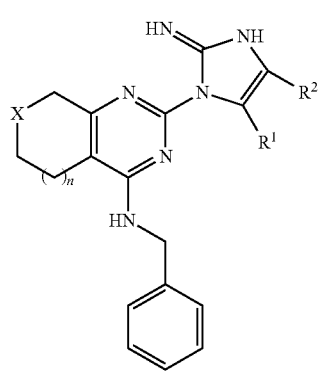

Formula LXIII

For Formula LXIII above, $R^1$ and $R^2$ vary independently. $R^1$ and $R^2$ independently selected from H, Me, Et, Pr, and Bu. n is −1, 0, 1, or 2. X is selected from $CH_2$, O, NMe, NEt, NPh at any position in the ring. A compound of Formula LXIII can be synthesized following a scheme as shown in Example 4.

In another example, a compound derivative is represented by Formula LXIV:

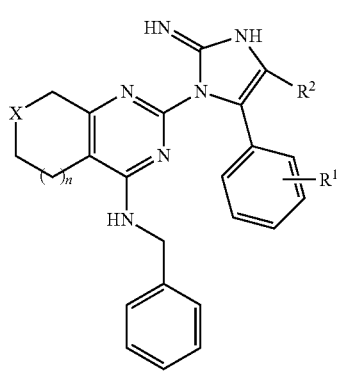

Formula LXIV

For Formula LXIV, R¹ is selected from H, Me, F, Cl, Br, and OMe at any position on the ring. R² is selected from H, Me, Et, Pr, and Bu. X is selected from CH$_2$, O, NMe, NEt, and NPh at any position on the ring. n is −1, 0, 1, or 2. A compound of Formula LXIV can be synthesized following a scheme as shown in Example 4.

In another example, a compound derivative is represented by Formula LXV:

Formula LXV

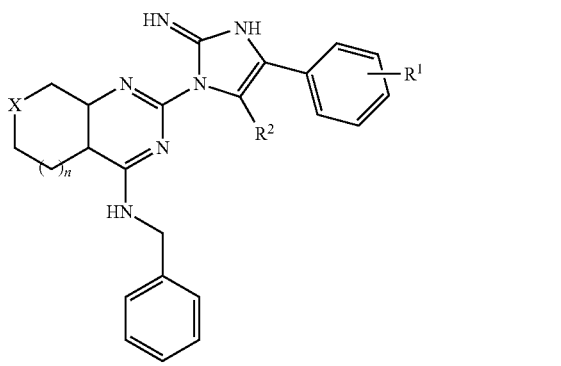

For Formula LXV, R¹ is selected from H, Me, F, Cl, Br, and OMe at any position on the ring. R² is selected from H, Me, Et, Pr, and Bu. X is selected from CH$_2$, O, NMe, NEt, and NPh at any position on the ring. n is −1, 0, 1, or 2. A compound of Formula LXV can be synthesized following a scheme as shown in Example 4.

In another example, a compound derivative is represented by Formula LXVI:

Formula LXVI

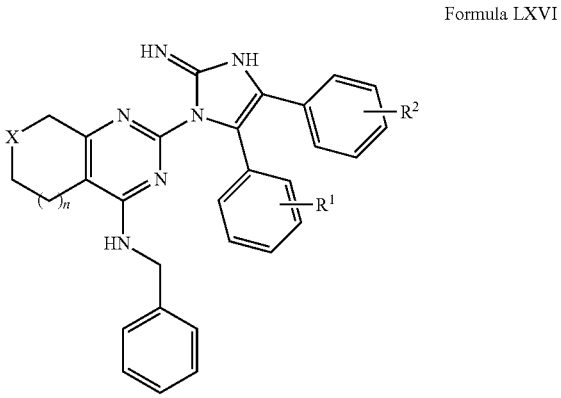

For Formula LXVI, R¹ and R² can vary independently. R¹ and R² are independently selected from H, Me, F, Cl, Br, and OMe at any position on the ring. X is selected from CH$_2$, O, NMe, NEt, and NPh at any position on the ring. n is −1, 0, 1, or 2. A compound of Formula LXVI can be synthesized following a scheme as shown in Example 4.

Isomers

Compounds of this invention may contain asymmetrically substituted carbon atoms in the R or S configuration, wherein the terms "R" and "S" are as defined in *Pure Appl. Chem.* (1976) 45, 11-30. Compounds having asymmetrically substituted carbon atoms with equal amounts of R and S configurations are racemic at those atoms. Atoms having excess of one configuration over the other are assigned the configuration in excess, preferably an excess of about 85%-90%, more preferably an excess of about 95%-99%, and still more preferably an excess greater than about 99%. Accordingly, this invention is meant to embrace racemic mixtures and relative and absolute diastereoisomers of the compounds thereof.

Compounds of this invention may also contain carbon-carbon double bonds or carbon-nitrogen double bonds in the Z or E configuration, in which the term "Z" represents the larger two substituents on the same side of a carbon-carbon or carbon-nitrogen double bond and the term "E" represents the larger two substituents on opposite sides of a carbon-carbon or carbon-nitrogen double bond. The compounds of this invention may also exist as a mixture of "Z" and "E" isomers.

Compounds of this invention may also exist as tautomers or equilibrium mixtures thereof wherein a proton of a compound shifts from one atom to another. Examples of tautomers include, but are not limited to, keto-enol, phenol-keto, oxime-nitroso, nitro-aci, imine-enamine and the like.

In one embodiment, isomers of the disclosed compounds are regioisomers or stereoisomers.

Compound Analogs

The compounds disclosed herein may be further modified to enhance solubility, detection and/or delivery in the body. The following modifications are not necessarily exclusive to another and can be combined. For example, a PEGylated and fluorescently labeled compound is disclosed.

In one embodiment, a compound of the present invention is fluorescently labeled. Suitable fluorescent labels are well known. A fluorescent label to be added to an inhibitor compound includes, but is not limited to, NBD-Cl (4-Chloro-7-nitro-2,1,3-benzoxadiazole), R—NCO (isocyanate), R—NCS (FITC).

In one embodiment, a compound of the present invention is biotinylated. Biotinylation is carried out using a biotin derivative. Examples of biotin derivatives include ester-biotin, amine-biotin, amide-biotin, and OH-biotin.

In one embodiment, a compound of the present invention is PEGylated with at least one PEG moiety. It is well known in the art that polyalkylene glycols, such as polyethylene glycol (PEG), may be attached to a therapeutic agent. Polyalkylene glycolated (PAGylated) therapeutic agents, and in particular, PEGylated therapeutic agents, have been reported to increase solubility, circulating life, safety, decrease renal excretion, and decrease immunogenicity thus potentially providing a method of improved drug delivery. A PEGylated therapeutic agent may exhibit (a) increased plasma circulatory half lives in vivo compared to the corresponding non-PEGylated compound, (b) enhanced therapeutic indices compared to the corresponding non-PEGylated compounds and (c) increased solubility compared to the corresponding non-PEGylated compounds, effecting possible improved drug delivery. Examples in which PEGylation has been used to effect drug delivery are disclosed, for example, in U.S. Pat. Nos. 6,623,729, 6,517,824, 6,515,017, 6,217,869, 6,191,105, 5,681,811, 5,455,027, U.S. Published Patent Application Nos. 20040018960, 20030229010, 20030229006, 20030186869, 20030026764, and 20030017131 U.S. Pat. No. 6,214,966, U.S. Published Patent Application No 2003000447, and U.S. Published Patent Application No. 2001021763 describe soluble, degradable poly(ethylene glycol) derivatives for controlled release of bound molecules into solution. Recent reviews on PEGylation are provided in, for example, Greenwald R. B., Choe Y. H., McGuire J., Conover C D. Adv. Drug Del. Rev. 2003, 55, 217, Molineux G. Pharmacotherapy 2003, (8 Pt 2), 3S-8S, Roberts M. J., Bentley, M. D., Harris J. M. Adv. Drug Deliv. Rev. 2002, 54, 459, Bhadra D., Bhadra S., Jain P., Jain N. K. Pharmazie 2002, 57, 5, Greenwald R B.

J. Controlled Release 2001, 74, 159, Veronese F. M., Morpurgo M. Farmaco. 1999, 54, 497 and Zalipsky S. Adv. Drug Deliv. Rev. 1995, 76, 157. In particular, the compounds of formulas I through LXVI as described herein, may be PEGylated.

Pharmaceutical Salts

The phrase "pharmaceutically acceptable" is used herein to refer to those compounds, materials, compositions, and/or dosage forms which are, within the scope of the medical arts, suitable for use in contact with the tissues of human beings and animals without excessive toxicity, irritation, allergic response, or other problem or complication, commensurate with a reasonable benefit/risk ratio.

Compounds of the present invention, including all analogs and isomers of the compounds may exist as acid addition salts, basic addition salts or zwitterions. Salts of compounds disclosed herein are prepared during their isolation or following their purification. Acid addition salts are those derived from the reaction of a compound of the present invention with acid. Accordingly, salts including the acetate, adipate, alginate, bicarbonate, citrate, aspartate, benzoate, benzenesulfonate (besylate), bisulfate, butyrate, camphorate, camphorsulfonate, digluconate, formate, fumarate, glycerophosphate, glutamate, hemisulfate, heptanoate, hexanoate, hydrochloride, hydrobromide, hydroiodide, lactobionate, lactate, maleate, mesitylenesulfonate, methanesulfonate, naphthylenesulfonate, nicotinate, oxalate, pamoate, pectinate, persulfate, phosphate, picrate, propionate, succinate, tartrate, thiocyanate, trichloroacetic, trifluoroacetic, para-toluenesulfonate and undecanoate salts of the compounds having any of formulas I through LXVI are meant to be embraced by this invention. Basic addition salts of compounds are those derived from the reaction of the compounds with the bicarbonate, carbonate, hydroxide or phosphate of cations such as lithium, sodium, potassium, calcium and magnesium. Lists of suitable salts are found in Remington's Pharmaceutical Sciences, 17th ed., Mack Publishing Company, Easton, Pa., 1985, p. 1418 and in the Journal of Pharmaceutical Science, 66, 2 (1977), the disclosures of each of which are hereby incorporated by reference.

Pharmaceutical Formulations and Dosage Forms

When employed as pharmaceuticals, the compounds of any of Formulas (I-LXVI) can be administered in the form of pharmaceutical compositions. These compositions can be administered by a variety of routes including oral, rectal, transdermal, subcutaneous, intravenous, intramuscular, and intranasal, and can be prepared in a manner well known in the pharmaceutical art.

This invention also includes pharmaceutical compositions which contain, as the active ingredient, one or more of the compounds of Formulas I-LXVI (including analogs and isomers thereof) above in combination with one or more pharmaceutically acceptable carriers. In making the compositions of the invention, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions in can be nebulized by use of inert gases. Nebulized solutions may be breathed directly from the nebulizing device or the nebulizing device can be attached to a face masks tent, or intermittent positive pressure breathing machine. Solution, suspension, or powder compositions can be administered orally or nasally from devices which deliver the formulation in an appropriate manner.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. An amount adequate to accomplish this is referred to as "therapeutically effective amount." Effective doses will depend on the disease condition being treated as well as by the judgement of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

Compounds disclosed herein may be administered, for example, bucally, ophthalmically, orally, osmotically, parenterally (intramuscularly, intraperintoneally intrasternally, intravenously, subcutaneously), rectally, topically, transdermally, vaginally and intraarterially as well as by intraarticular injection, infusion, and placement in the body, such as, for example, the vasculature by means of, for example, a stent.

The present invention also includes pharmaceutical kits useful, for example, in the treatment of cancers, which comprise one or more containers containing a pharmaceutical composition comprising a therapeutically effective amount of a compound of Formula (I-LXVI). Such kits can further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

EXAMPLES

Example 1

Purchased Compounds

Compounds shown in Tables 1-33 were either synthesized or purchased as indicated in the Tables, wherein S indicates synthesized and P indicates purchased. Table 34 below provides company information for purchased compounds.

TABLE 34

| Cpd # | KU SCC # | Company |
|---|---|---|
| I-1 | KSC-1-150 | Chembridge |
| I-2 | KSC-1-145 | Aldrich |
| I-3 | KSC-1-146 | Chembridge |
| I-4 | KSC-1-149 | Chembridge |
| I-5 | KSC-1-226 | Chemdiv |
| I-6 | KSC-1-236 | Princeton Biomecular Research, Inc |
| I-7 | KSC-1-147 | Chembridge |
| I-8 | KSC-1-234 | Princeton Biomecular Research, Inc |
| I-9 | KSC-1-227 | Chemdiv |
| I-10 | KSC-1-224 | Chemdiv |
| I-11 | KSC-1-200 | Ryan Scientific, Inc. |
| I-12 | KSC-1-211 | Ryan Scientific |
| I-13 | KSC-1-212 | Ryan Scientific |
| I-14 | KSC-1-214 | Ryan Scientific |
| I-15 | KSC-1-215 | Ryan Scientific |
| I-16 | KSC-1-217 | Chemdiv |
| I-17 | KSC-1-219 | Chemdiv |
| I-20 | KSC-1-220 | Chemdiv |
| I-21 | KSC-1-221 | Chemdiv |
| I-22 | KSC-1-222 | Chemdiv |
| I-23 | KSC-1-223 | Chemdiv |
| I-24 | KSC-1-225 | Chemdiv |
| I-25 | KSC-1-258 | Interchim |
| I-26 | KSC-1-218 | Chemdiv |
| I-27 | KSC-1-148 | Chembridge |
| I-28 | KSC-1-235 | Princeton Biomecular Research, Inc |
| I-29 | KSC-1-238 | Princeton Biomecular Research, Inc |
| I-30 | KSC-1-237 | Princeton Biomecular Research, Inc |
| I-31 | KSC-1-216 | Chemdiv |
| I-32 | KSC-1-193 | Albany Molecular Research, Inc. |
| I-33 | KSC-1-194 | Albany Molecular Research |
| I-34 | KSC-1-195 | Albany Molecular Research |
| I-35 | KSC-1-213 | Ryan Scientific |
| XXII | KSC-1-152 | Chembridge |

TABLE 34-continued

| Cpd # | KU SCC # | Company |
|---|---|---|
| XLIV | KSC-1-151 | Chembridge |
| XLV | KSC-1-260 | interchim |
| XLVI | KSC-1-240 | Princeton Biomecular Research, Inc |
| XLVII | KSC-1-208 | Ryan Scientific |
| XLVIII | KSC-1-241 | Princeton Biomecular Research, Inc |
| XXIII | KSC-1-203 | Ryan Scientific |
| XLIX | KSC-1-239 | Princeton Biomecular Research |
| L | KSC-1-242 | Princeton Biomecular Research |
| LI | KSC-1-254 | Princeton Biomecular Research, Inc |
| II-1 | KSC-1-153 | Chembridge |
| II-2 | KSC-1-251 | Princeton Biomecular Research |
| II-3 | KSC-1-246 | Princeton Biomecular Research |
| II-4 | KSC-1-249 | Princeton Biomecular Research |
| II-5 | KSC-1-245 | Princeton Biomecular Research |
| II-6 | KSC-1-250 | Princeton Biomecular Research |
| II-7 | KSC-1-252 | Princeton Biomecular Research |
| II-9 | KSC-1-247 | Princeton Biomecular Research |
| II-11 | KSC-1-248 | Princeton Biomecular Research |
| II-12 | KSC-1-253 | Princeton Biomecular Research |
| II-13 | KSC-1-244 | Princeton Biomecular Research |
| II-17 | KSC-1-259 | interchim |

Example 2

Compound Synthesis

In general, compounds of the invention, including salts and solvates thereof, can be prepared using known organic synthesis techniques and can be synthesized according to any of numerous possible synthetic routes. The reactions for preparing compounds of the invention can be carried out in suitable solvents which can be readily selected by one of skill in the art of organic synthesis. Suitable solvents can be substantially nonreactive with the starting materials (reactants), the intermediates, or products at the temperatures at which the reactions are carried out, i.e., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected.

Preparation of compounds of the invention can involve the protection and deprotection of various chemical groups. The need for protection and deprotection, and the selection of appropriate protecting groups can be readily determined by one skilled in the art. The chemistry of protecting groups can be found, for example, in T. W. Greene and P. G. M. Wuts, Protective Groups in Organic Synthesis, 3rd. Ed., Wiley & Sons, Inc., New York (1999), which is incorporated herein by reference in its entirety.

Reactions can be monitored according to any suitable method known in the art. For example, product formation can be monitored by spectroscopic means, such as nuclear magnetic resonance spectroscopy (e.g., $^1$H or $^{13}$C) infrared spectroscopy, spectrophotometry (e.g., UV-visible), or mass spectrometry, or by chromatography such as high performance liquid chromatography (HPLC) or thin layer chromatography.

Synthesized compounds were synthesized using one of the following three synthesis schemes. Synthesis scheme I was carried out with reference to Gavish et al. WO 2008/023357A1.

Synthesis Scheme I:

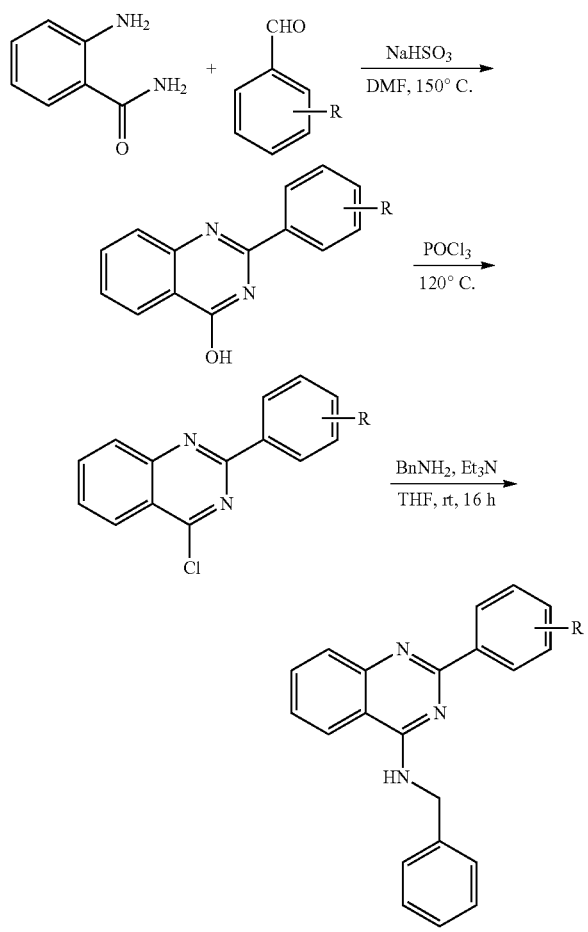

Synthesis scheme II was carried out with reference to Gahman et al. US 2009/0209536 A1.

Synthesis Scheme II:

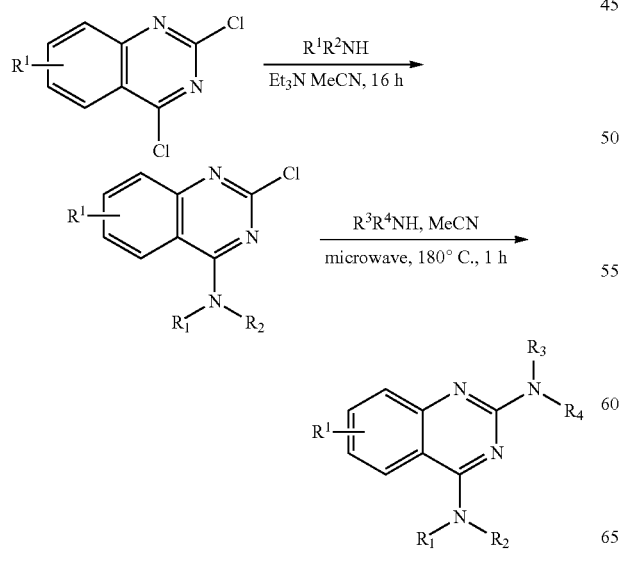

Synthesis Scheme III:

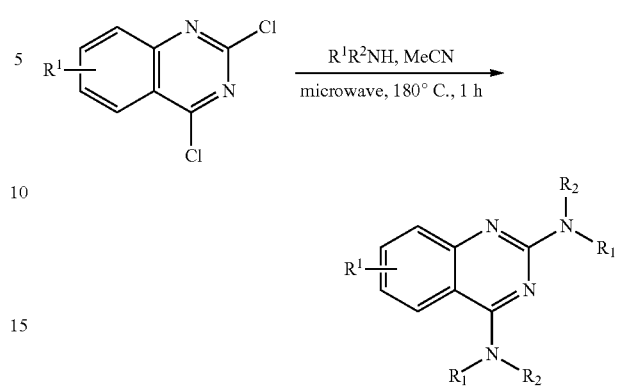

Representative compound synthesis: N2,N4-dibenzyl-8-methoxyquinazoline-2,4-diamine. (Compound #VI-5). To a suspension of 2,4-dichloro-8-methoxyquinazoline (50 mg, 0.22 mmol) in acetonitrile (1 mL) was added benzylamine (0.12 mL, 1.09 mmol, 5 equiv.). The mixture was heated to 180° C. for 1 h under microwave irradiation. The concentrated residue was purified by silica gel chromatography (Ethyl acetate) to give a white solid. $^1$H NMR (400 MHz, CDCl$_3$) δ 7.44-7.18 (m, 11H), 7.11 (dd, J=1.6, 7.9 Hz, 1H), 7.07-6.93 (m, 2H), 5.86 (s, br. 1H), 5.49 (s, br. 1H), 4.78 (d, J=5.7 Hz, 2H), 4.75 (d, J=5.7 Hz, 2H), 3.99 (s, 3H). $^{13}$C NMR (101 MHz, CDCl$_3$) δ 160.1, 159.3, 153.2, 144.2, 140.2, 138.7, 128.7, 128.4, 128.0, 127.5, 126.8, 120.4, 112.5, 111.2, 110.9, 55.9, 45.7, 45.2. HRMS (m/z): calcd for $C_{23}H_{23}N_4O$ (M+H) 371.1872; found 371.1871.

Some specific examples of synthesis schemes are shown as follows.

Specifically, for XXIV, the synthesis scheme is as shown below:

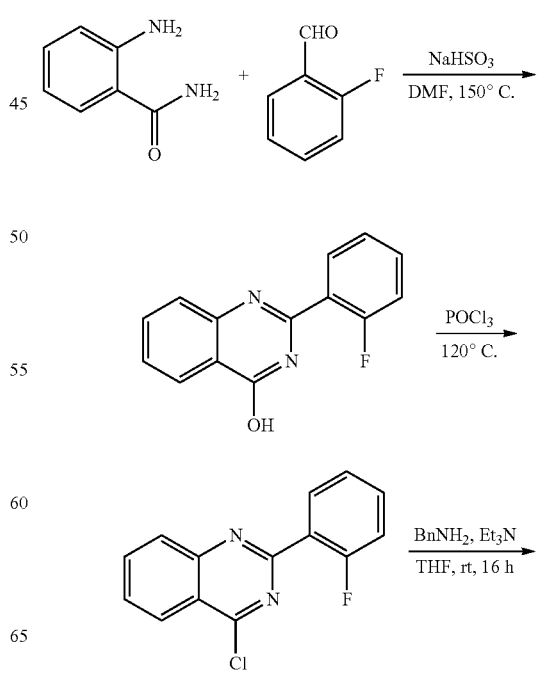

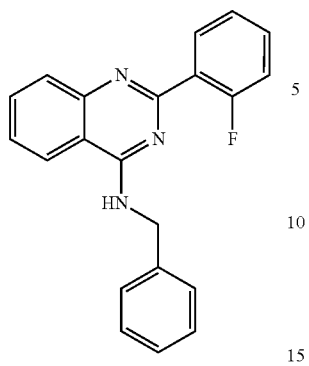
A synthesis scheme for Formula II is shown below:
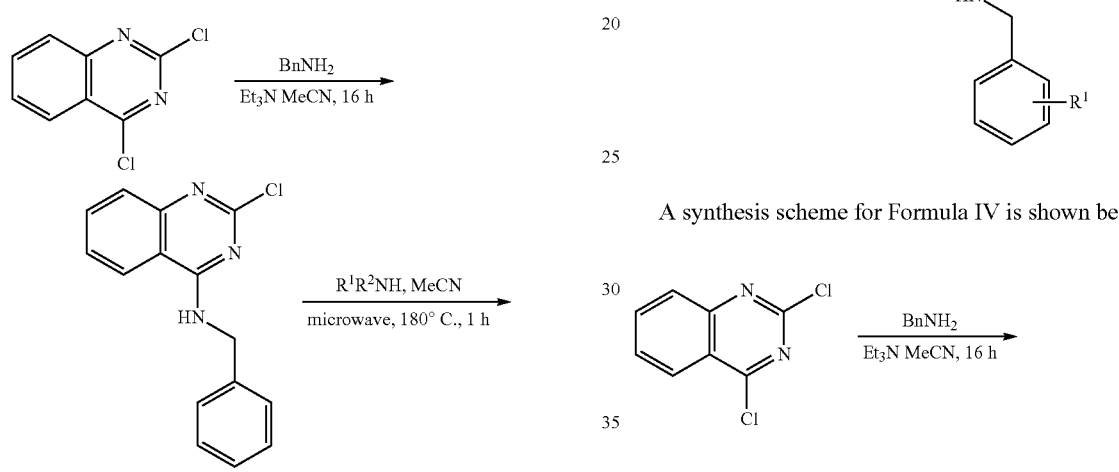
A synthesis scheme for Formula III is shown below:
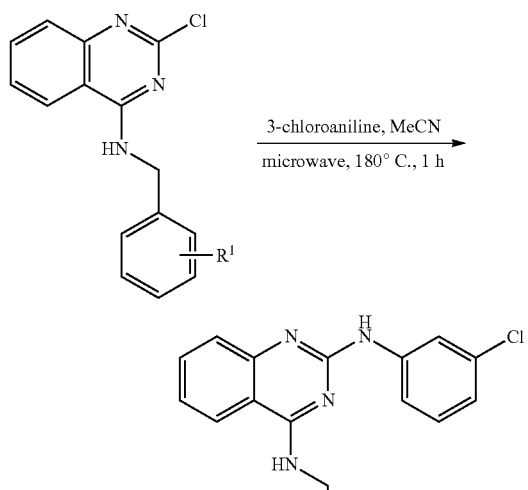
A synthesis scheme for Formula IV is shown below:
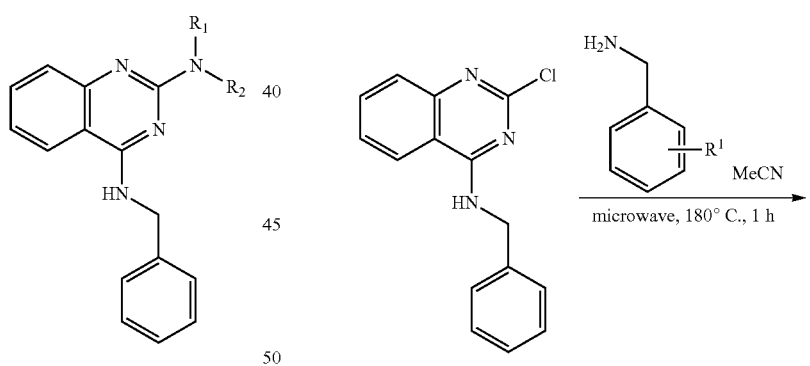
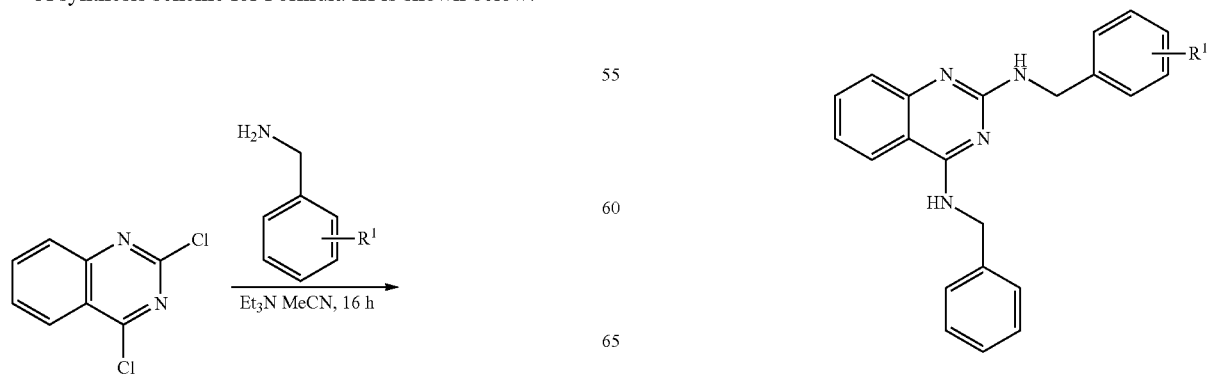

A synthesis scheme for Formula V is shown below:
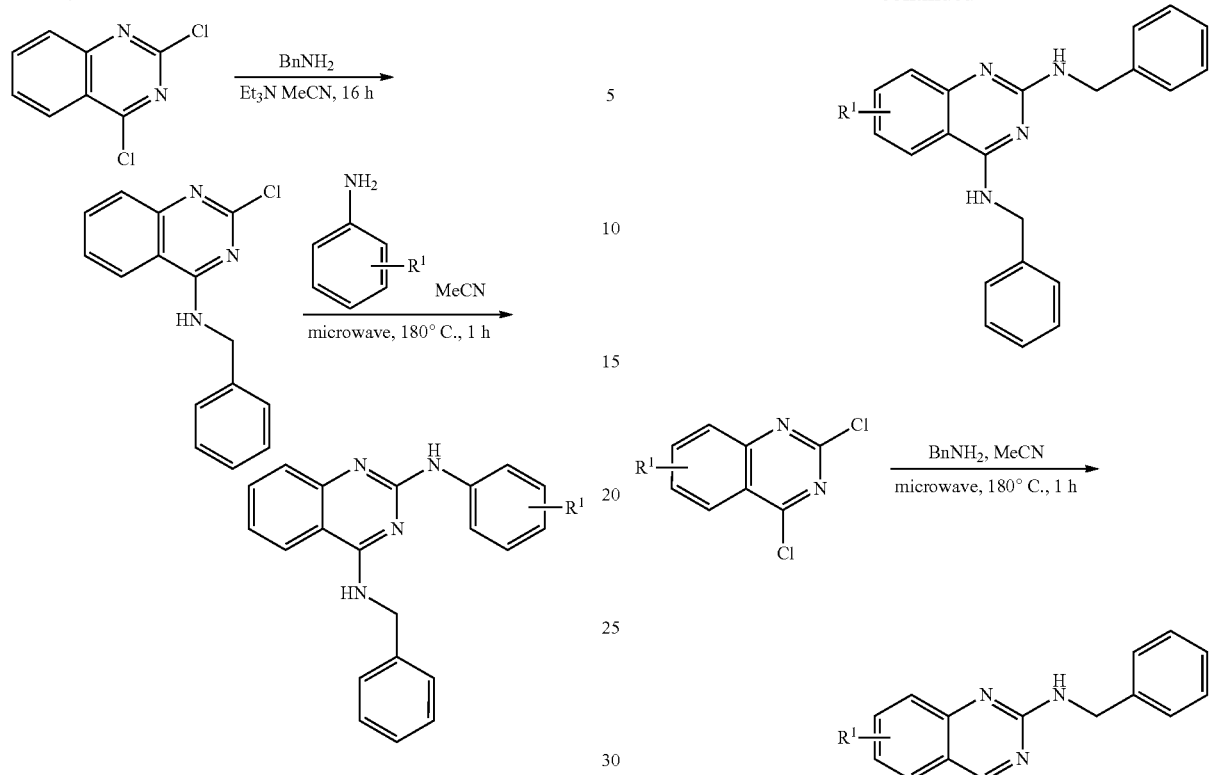
A synthesis scheme for Formula VI is shown below:
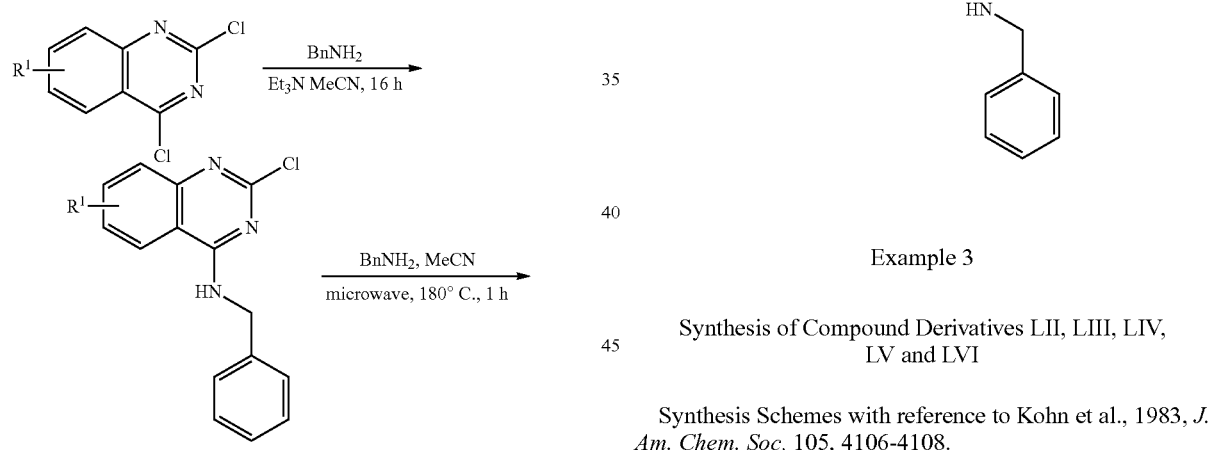
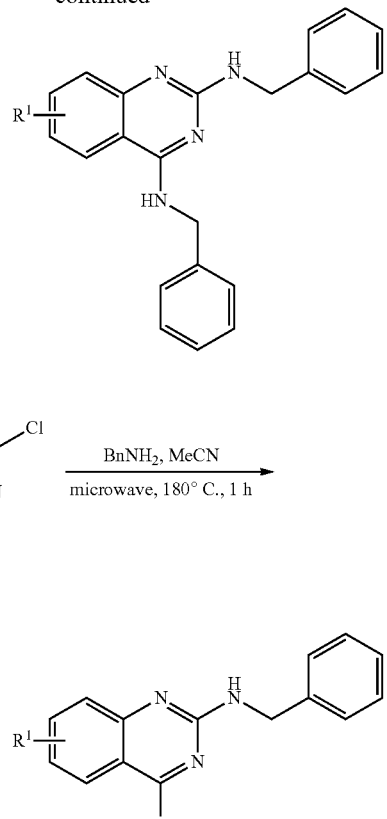
Example 3
Synthesis of Compound Derivatives LII, LIII, LIV, LV and LVI
Synthesis Schemes with reference to Kohn et al., 1983, *J. Am. Chem. Soc*, 105, 4106-4108.
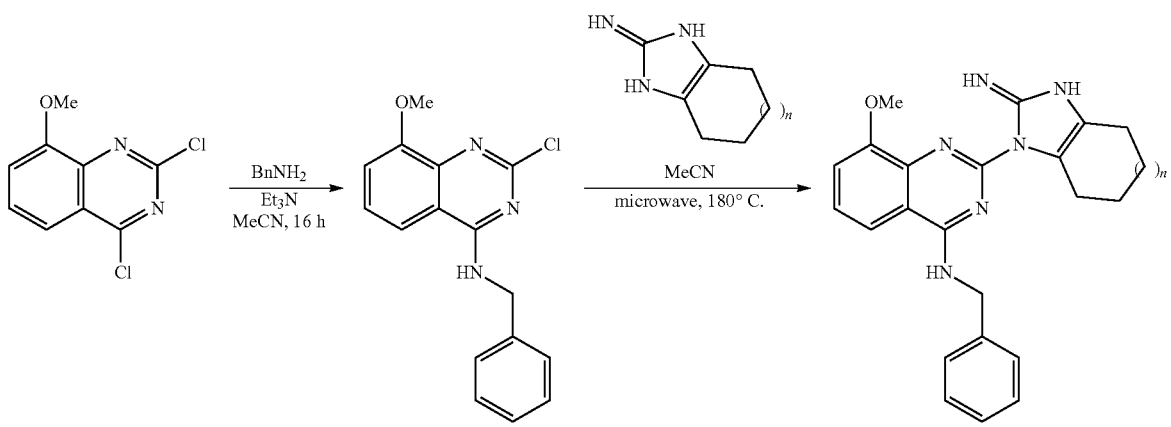

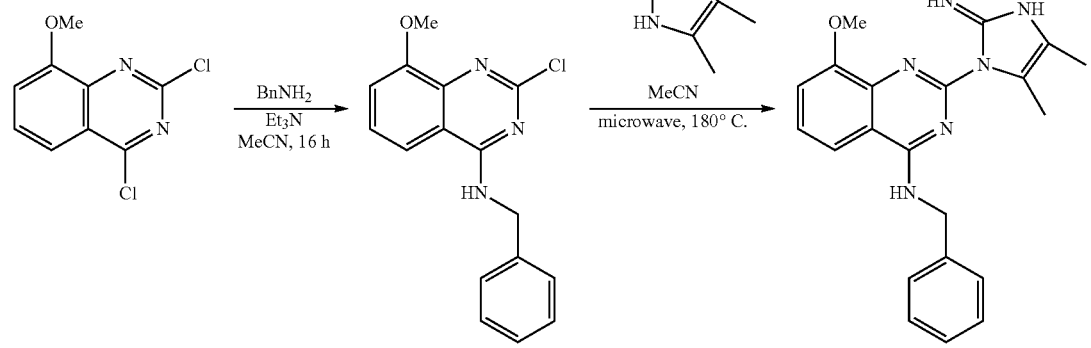
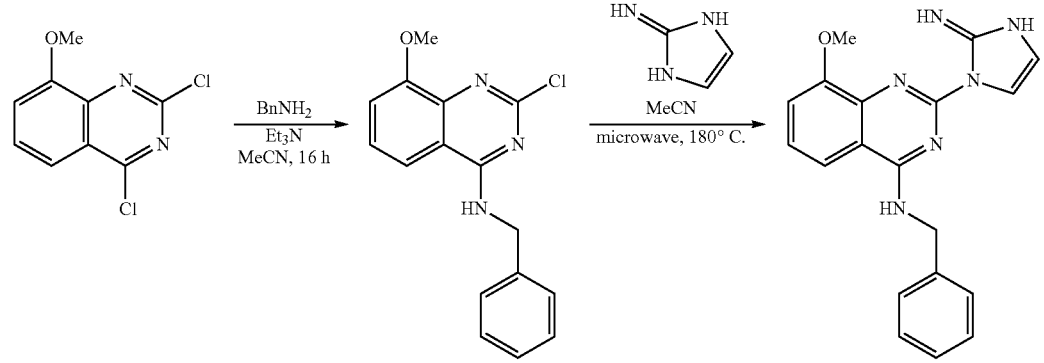
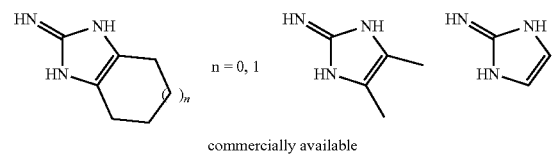
commercially available
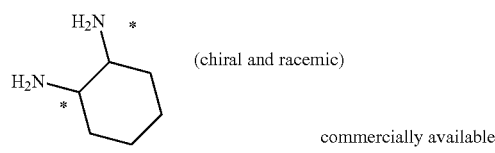
(chiral and racemic)
commercially available
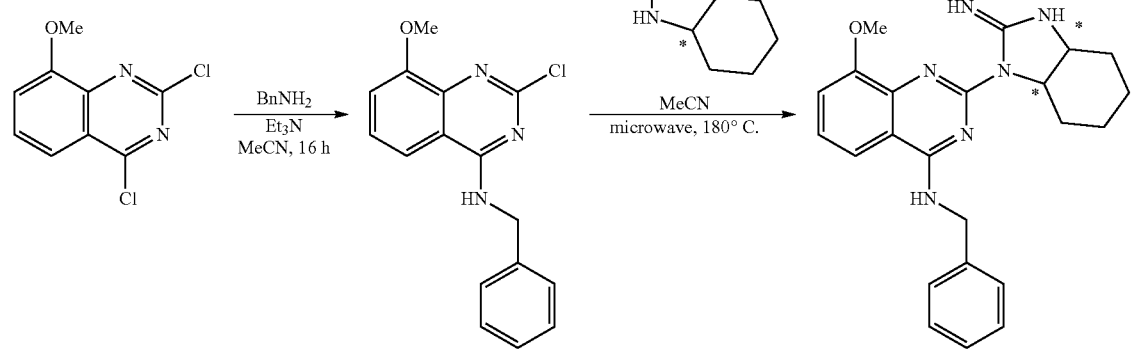
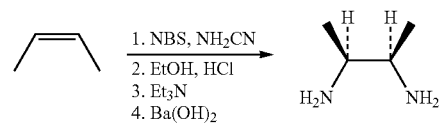

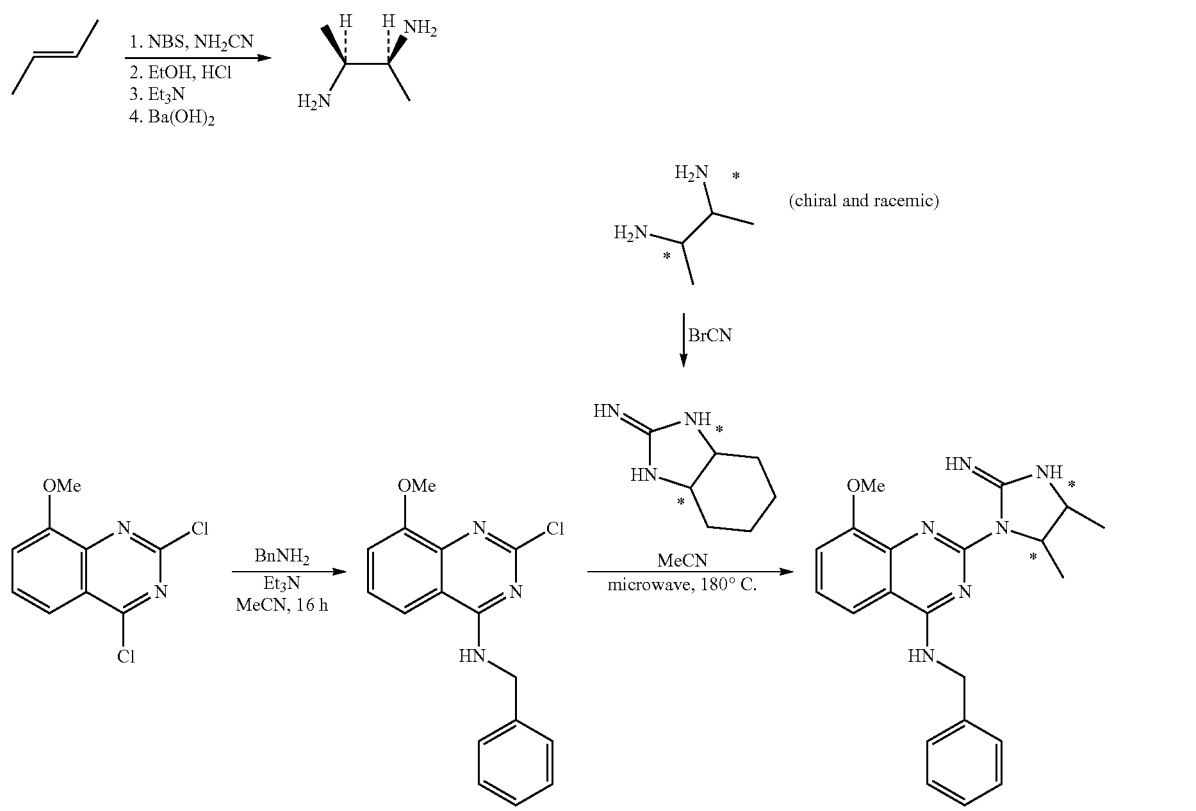
Example 4
Synthesis of Compound Derivatives LVII, LVIII, LXII, LXIII, LXIV, LXV, and LXVI
Synthesis scheme for LVII. For LVIII and LXII-LXVI, reference is made to the scheme below, with reference to schemes disclosed herein and Zaugg, 1984, *Synthesis*, 86-110.
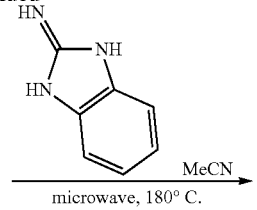
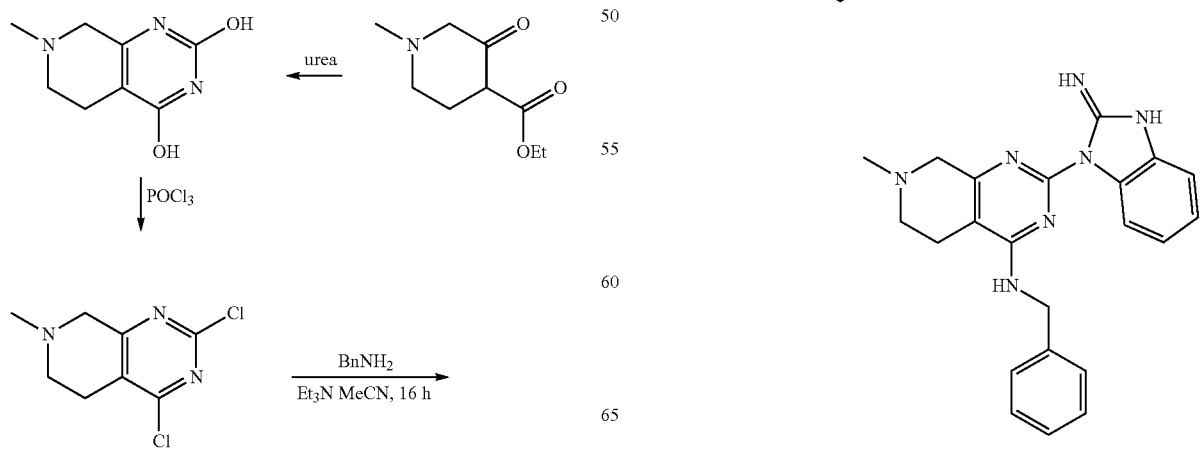

Example 5
Synthesis of Compound Derivatives LIX and LXI
Synthesis scheme for LIX with reference to Tikad et al., 2006, *Synlett*, 1938-1942.
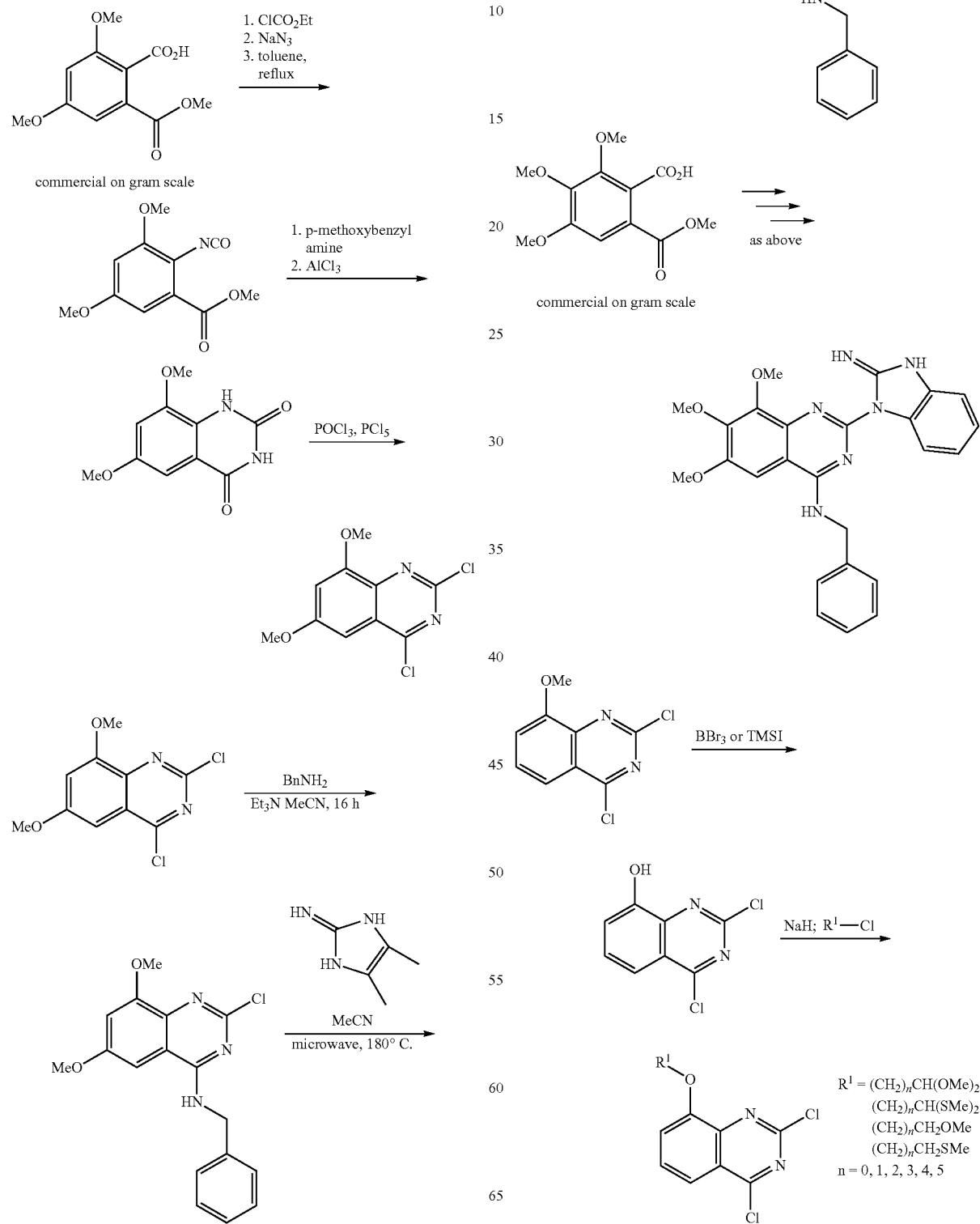

85
-continued
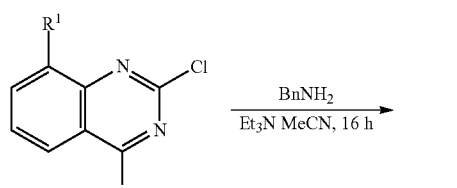
R[1] defined above
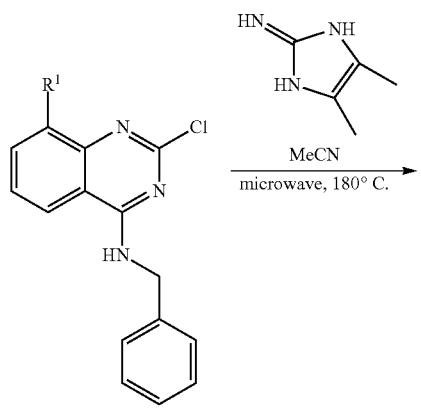
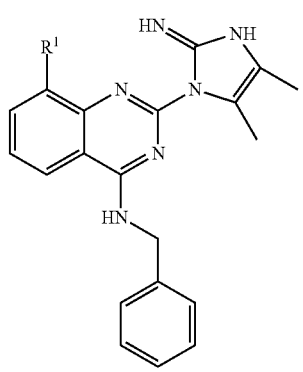
Synthesis scheme for LX with reference to above reaction and reference for LIX.
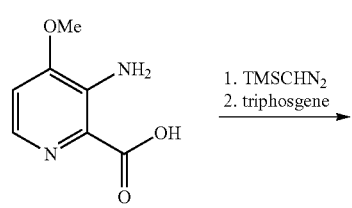
commercial on gram scale
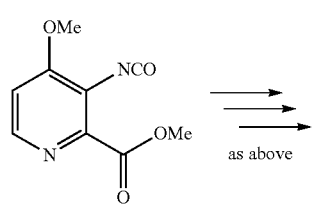
86
-continued
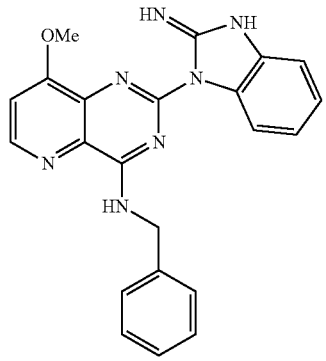
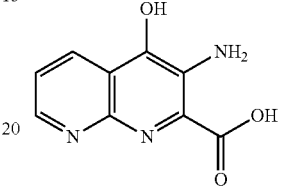
commercial on gram scale
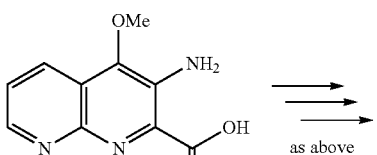
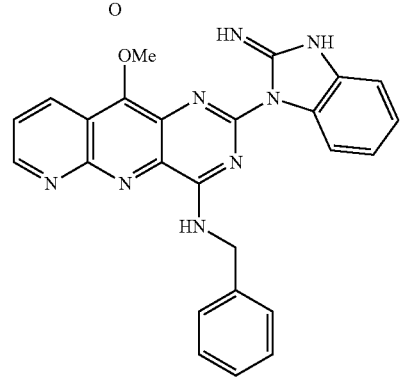
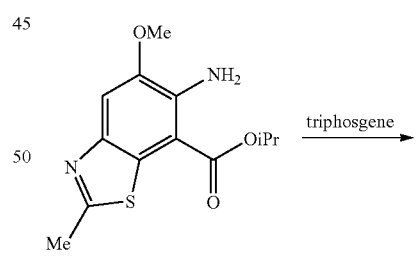
commercial on gram scale
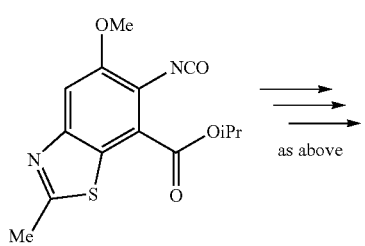

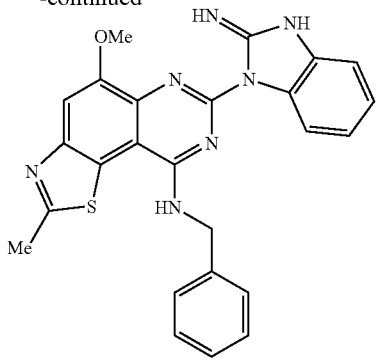

Example 6

Synthesis of Compound Derivative LXI

Synthesis scheme for LXI with reference to Zaugg, 1984, *Synthesis*, 86-110.

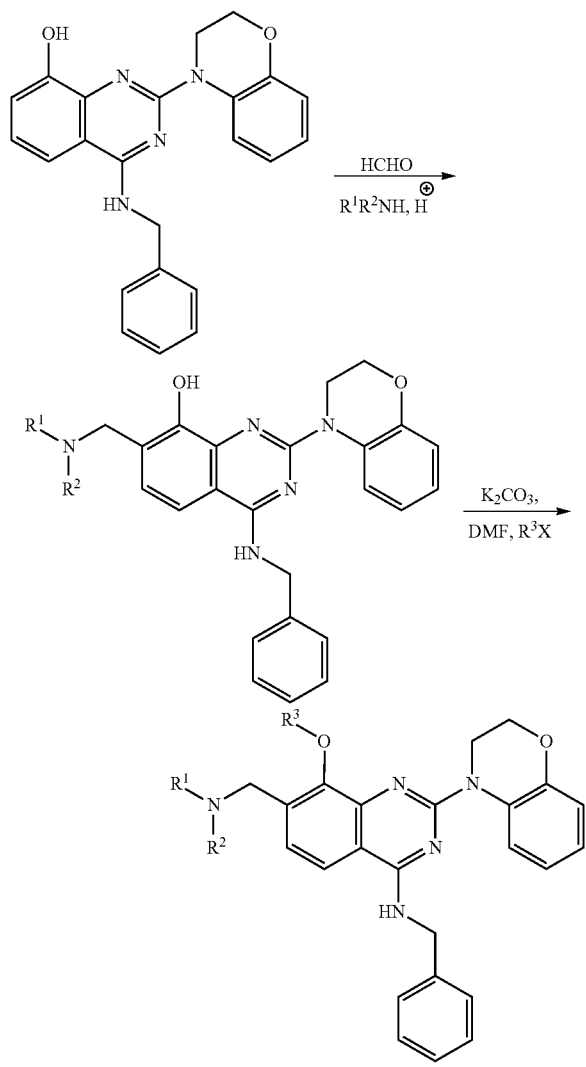

Example 7

ATPase Assay

Assay Buffer (20 μL of 2.5× concentration, where 1×=50 mM Tris pH 7.4, 20 mM $MgCl_2$, 1 mM EDTA, 0.5 mM TCEP) was dispensed into each well of a 96 well plate. Purified p97 (25 μL of 50 μM) was diluted in 975 μL, of 1× Assay Buffer and 10 μL was dispensed in each well. Test compound (10 μL) or 5% DMSO (10 μL) was then added to each well and the plate was incubated at room temperature for 10 min. The ATPase assay was carried out by adding to each well 10 μL of 500 μM ATP (pH 7.5), incubating at room temperature for 60 min, and then adding 50 μL Kinase Glo Plus reagent (Promega) followed by a final 10 min incubation at room temperature in the dark. Luminescence was read on an Analyst AD (Molecular Devices). Compounds were assayed at a range of concentrations (0, 0.048, 0.24, 1.2, 6, 30 μM) in triplicate. The percent of remaining activity for each reaction was calculated using the following mathematical expression: ((Test Compound−High Control)/(Low Control−High Control))*100. Test_Compound is defined as wells containing test compound, Low_Control is defined as wells containing DMSO, High_Control is defined as wells containing no p97 protein. $IC_{50}$ values were calculated from fitting the percentage of remaining activity (% RA) with various concentrations of compounds to a Langmuir equation [% RA=100/(1+[Compound]/$IC_{50}$)] by non-linear regression analysis using the JUMP IN program. The result was expressed as mean +/− standard error. For assays with Myriad 12 and 19, 100 μL of biomol green reagent (Enzo Life Sciences) was added to each well instead of kinase Glo Plus (Promega) and absorbance at 630 nm was measured. This was done because these compounds interfered with luciferase activity. For assays with compounds that interfered with luciferase activity, 100 μL of biomol green reagent (Enzo Life Sciences) was added to each well instead of kinase Glo Plus (Promega) and absorbance at 630 nm was measured.

Example 8

$Ub^{G76V}$-GFP Degradation Assay

Two GFP images with 100 ms exposure time per well were acquired and the average GFP intensity per area of a HeLa cell was determined by using MetaXpress software. Mean GFP intensity of 300-500 cells was calculated using Excel. Normalized GFP intensity was calculated using the following formula: (Test compound−Background)/(Basal GFP intensity—Background). Where: Test compound is defined as Mean GFP intensity of $Ub^{G76V}$-GFP-expressing cells treated with the test compound. Background is defined as background GFP intensity of HeLa cells. Basal GFP intensity is defined as mean GFP intensity of $Ub^{G76V}$-GFP-expressing cells treated with DMSO. The degradation rate constant (k) was obtained from the slope of the linear range of plotting Ln (Normalized GFP intensity) versus time ranging from 90 to 180 min. The percent of remaining k for each compound is calculated using the following formula: (Test compound/DMSO control)*100. Where: Test_compound is defined as k determined from wells containing test compound, DMSO control is defined as k determined from wells containing DMSO. $IC_{50}$ values were calculated from fitting the percentage of remaining k (% k) with various concentrations of compounds to a Langmuir equation [% k=100/(1+[Compound]/IC$_{50}$)] by non-linear regression analysis using the JUMP IN program. The result was expressed as mean +/- standard error.

Example 9

NMR Analysis of Compounds

NMR data for all compounds in attached in the Appendix.

$^1$H and $^{13}$C spectra were recorded on a Bruker Avance 400 or 500 MHz spectrometer. Chemical shifts are reported in parts per million and were referenced to residual proton solvent signals.

What is claimed is:

1. A composition suitable for decreasing p97 ATPase activity and/or degradation of a p97 dependent ubiquitin-proteasome substrate, comprising: a compound of Formula VII, IX, XII, XX, XXI or XLIII, or a pegylated analog of the compound, a pharmaceutically acceptable salt of the compound or the analog, or any regioisomer or stereoisomer of the compound:

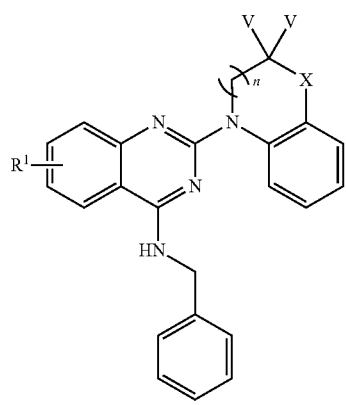

Formula VII

Wherein, for Formula VII, R$^1$, n, X, and Y are selected from the group consisting of combinations listed in Table 7:

TABLE 7

| Cpd # | R1 | n | X | Y |
|---|---|---|---|---|
| VII-3 | H | 1 | O | H, H |
| VII-4 | H | 1 | NH | H, H |
| VII-5 | 8-OMe | 1 | NH | H, H |
| VII-6 | 8-OMe | 1 | O | H, H |
| VII-7 | 8-OH | 1 | O | H, H |
| VII-8 | 8-Ph | 1 | O | H, H |
| VII-9 | 8-OCH$_2$CH$_2$OH | 1 | O | H, H |
| VII-10 | 8OCH$_2$CH$_2$NEt$_2$ | 1 | O | H, H |
| VII-11 | 8-p-OMePh | 1 | O | H, H |
| VII-12 | 8-OMe | 1 | NMe | H, H |
| VII-13 | 8-OMe | 1 | NCOMe | H, H |
| VII-14 | 8-OCH$_2$CH$_2$OMe | 1 | O | H, H |
| VII-16 | 8-OMe | 0 | NH | NH |
| VII-17 | 8-OMe | 0 | O | Y,Y together form one O as oxygen of carbonyl incorporating both Y's |
| VII-15 | 8-n-Butyl | 1 | O | H, H |

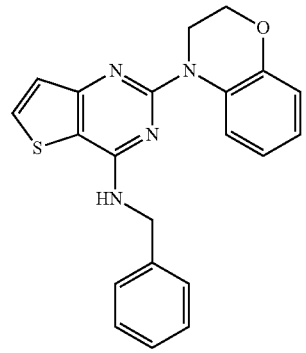

Formula IX

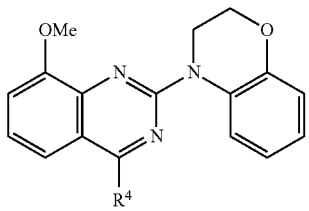

Formula XI

Wherein, for Formula XII, R$^4$ is selected from the group consisting of the moieties listed in Table 10:

TABLE 10.1

| Cpd # | R4 | Cpd # | R4 |
|---|---|---|---|
| XII-4 | HN—CH$_2$—C$_6$H$_4$—F (para) | XII-8 | HN—CH$_2$—C$_6$H$_4$—OH (ortho) |
| XII-7 | HN—CH$_2$—(2-pyridyl) | XII-10 | HN—CH$_2$—C$_6$H$_4$—OH (para) |
| XII-2 | HN—CH$_2$—C$_6$H$_4$—NMe$_2$ (meta) | XII-11 | N-benzoxazine |

TABLE 10.1-continued

| Cpd # | R4 | Cpd # | R4 |
|---|---|---|---|
| XII-9 | | | |

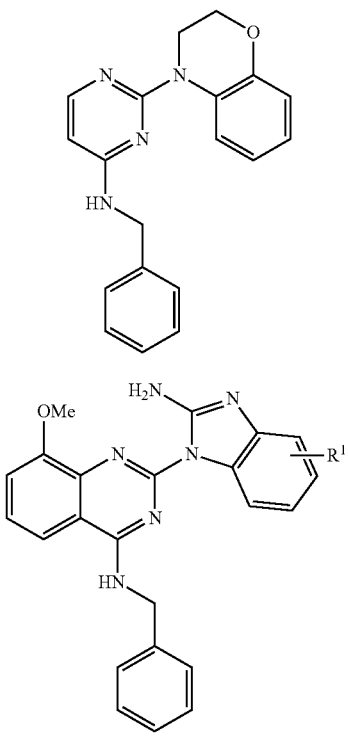

Formula XX

Formula XXI

Wherein for Formula XXI, R¹ is 5,6-dimethyl;

Formula XLIII

2. A composition of claim 1, further comprising a pharmaceutically acceptable carrier.

3. A composition of claim 1, wherein the isomer is a regioisomer or stereoisomer.

4. A composition of claim 1, wherein the compound is represented by Formula VII or XXI.

5. A composition of claim 4 wherein the compound is represented by Formula VII.

6. A composition suitable for decreasing p97 ATPase activity and/or degradation of a p97 dependent ubiquitin-proteasome substrate, comprising: a compound of Formula LII, LVII, LVIII, LIX, LX, LXI, LXII or a pegylated analog of the compound, a pharmaceutically acceptable salt of the compound or the analog, or any regioisomer or stereoisomer of the compound:

Formula LII wherein N is 0, 1 or 2;

Formula LVII wherein X is oxygen or N—R'
wherein R' is methyl, ethyl or phenyl; n is −1,
0, 1 or 2; m is 1, 2, 3 or 4; R¹ and R² are
independently selected from the group
consisting of hydrogen, methyl, fluoro, Chloro,
bromo and methoxy;

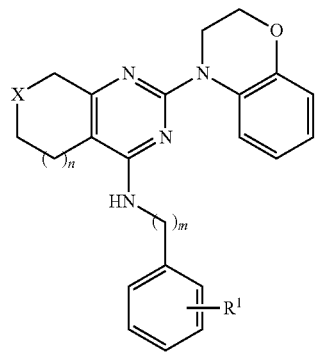

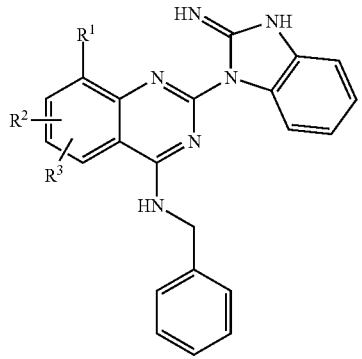

Formula LVIII wherein X is O, NR' wherein R' is methyl, ethyl or phenyl; n is −1, 0, 1 or 2; m is 1, 2, 3 or 4; $R^1$ is hydrogen, methyl fluoro, chloro, bromo or methoxy Formula LIX wherein $R^1$, $R^2$, $R^3$ are independently selected from the group consisting of hydrogen, $A(CH_2)_nCH_3$ and $A(CH_2)_nX$ wherein n is 0, 1, 2, 3, 4 or 5; A is O, S or NH; and X is heteroaryl, O-alkyl, S-alkyl, $(O\text{-alkyl})_2$ or $(S\text{-alkyl})_2$

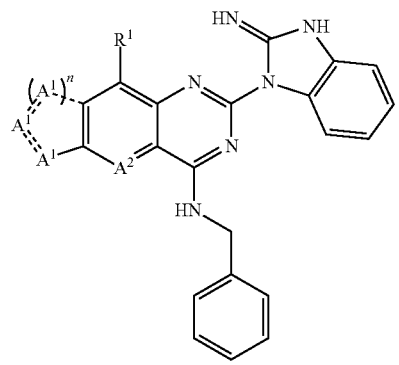

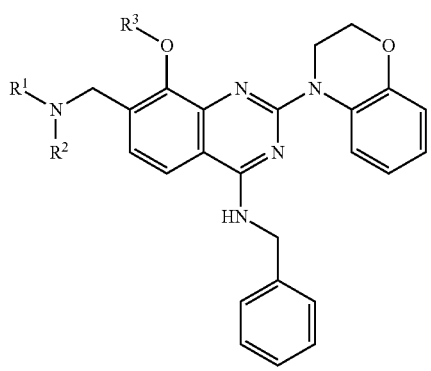

Formula LX wherein, $A^1$ is O, S, Se, N, NH, CH, $CH_2$, CHalkyl, or Calkyl; n is 1 or 2; $A^2$ is N, NH, CH, or Calkyl; and $R^1$ is selected from the group consisting of H, $A(CH_2)_mCH_3$, and $A(CH_2)_nX$, wherein A is O, S or NH and X is heteroaryl, O(alkyl), S(alkyl), $(O\text{-alkyl})_2$, or $(S\text{-alkyl})_2$; and m is 0, 1, 2, 3, 4, or 5

Formula LXI wherein $R^1$, $R^2$, $R^3$ are independently selected from the group consisting of alkyl, alkoxyalkyl and aminoalkyl

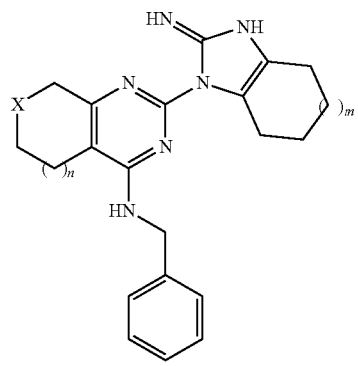

Formula LXII wherein n is −1, 0, 1 or 2; m is 0, 1 or 2; and X is $CH_2$, O or NR'; and R' is methyl, ethyl or phenyl.

7. A composition of claim 6, further comprising a pharmaceutically acceptable carrier.

8. A composition of claim 6, wherein the isomer is a regioisomer or stereoisomer.

9. A composition of claim 6, wherein the compound is represented by Formula LII, LVII, LVIII or LXII.

10. A composition of claim 6 wherein the compound is represented by Formula LVII, LVIII or LXII.

11. A composition of claim 6 wherein the compound has formula LIX-A

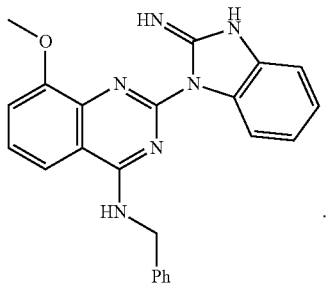

Formula LIX-A

12. A composition suitable for decreasing p97 ATPase activity and/or degradation of a p97 dependent ubiquitin-proteasome substrate, comprising: a compound of Formula VIII or a pegylated analog of the compound, a pharmaceutically acceptable salt of the compound or the analog, or any regioisomer or stereoisomer of the compound:

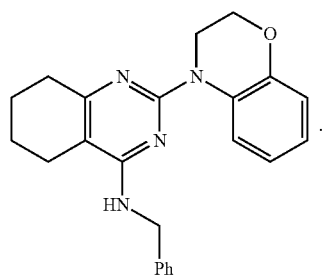

Formula VIII

13. A composition of claim 1 wherein the compound of Formula VII, IX, XII, XX, XXI or XLIII is labeled with a fluorescent label selected from the group consisting of 4-chloro-7-nitor-2,1,3-benzoxadiaxole, R—NCO wherein the R group is a stable organic fluorescent group and R—NCS wherein the R group is a stable organic fluorescent group.

14. A composition of claim 1 wherein the compound of Formula VII, IX, XII, XX, XXI or XLIII is biotinylated with a biotin derivative selected from the group consisting of ester-biotin, amin-biotin, amide-biotin and hydroxyl-biotin.

15. A composition of claim 6 wherein the compound of Formula LII, LVII, LVIII, LIX, LX, LXI, LXII is labeled with a fluorescent label selected from the group consisting of 4-chloro-7-nitor-2,1,3-benzoxadiaxole, R—NCO wherein the R group is a stable organic fluorescent group and R—NCS wherein the R group is a stable organic fluorescent group.

16. A composition of claim 6 wherein the compound of Formula LII, LVII, LVIII, LIX, LX, LXI, LXII is biotinylated with a biotin derivative selected from the group consisting of ester-biotin, amine-biotin, amide-biotin and hydroxyl-biotin.

17. A composition of claim 12 wherein the compound of Formula VIII is labeled with a fluorescent label selected from the group consisting of 4-chloro-7-nitor-2,1,3-benzoxadiaxole, R—NCO wherein the R group is a stable organic fluorescent group and R—NCS wherein the R group is a stable organic fluorescent group.

18. A composition of claim 12 wherein the compound of Formula VIII is biotinylated with a biotin derivative selected from the group consisting of ester-biotin, amin-biotin, amide-biotin and hydroxyl-biotin.

* * * * *

UNITED STATES PATENT AND TRADEMARK OFFICE
CERTIFICATE OF CORRECTION

PATENT NO. : 8,865,708 B2
APPLICATION NO. : 13/103003
DATED : October 21, 2014
INVENTOR(S) : Deshaies et al.

Page 1 of 2

It is certified that error appears in the above-identified patent and that said Letters Patent is hereby corrected as shown below:

In the Specification

In column 1, line 16-18, delete "This invention was made with government support under MH085687 awarded by National Institutes of Health. The government has certain rights in the invention." and insert --This invention was made with government support under Grant No. MH085687 and under Grant No. MH084512 awarded by the National Institutes of Health. The government has certain rights in the invention.--, therefor In the Claims In column 89, Formula VII, in Claim 1, delete " 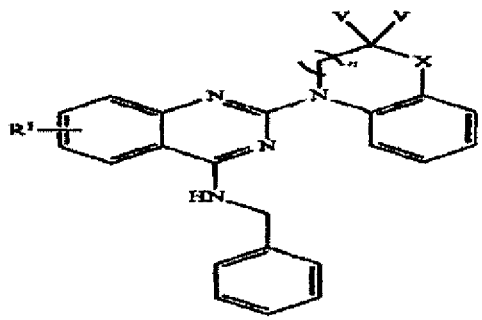 " and insert -- 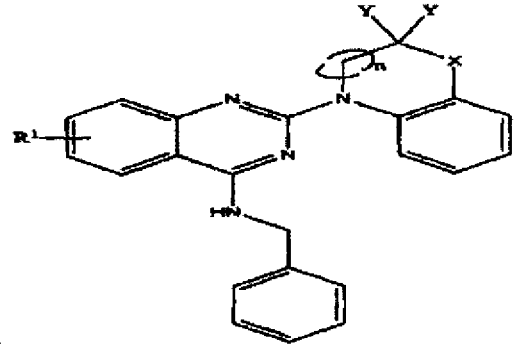 --, therefor Signed and Sealed this
Twenty-third Day of June, 2015

Michelle K. Lee
*Director of the United States Patent and Trademark Office*

CERTIFICATE OF CORRECTION (continued)
U.S. Pat. No. 8,865,708 B2

In column 89, line 50, table 1, in Claim 1, delete "Y" and insert --Y,Y--, therefor In column 90, line 16, in Claim 1, delete "XI" and insert --XII--, therefor

UNITED STATES PATENT AND TRADEMARK OFFICE
CERTIFICATE OF CORRECTION

| | | Page 1 of 1 |
|---|---|---|
| PATENT NO. | : 8,865,708 B2 | |
| APPLICATION NO. | : 13/103003 | |
| DATED | : October 21, 2014 | |
| INVENTOR(S) | : Deshaies et al. | |

It is certified that error appears in the above-identified patent and that said Letters Patent is hereby corrected as shown below:

Specification

In column 1, line 16-18, delete "This invention was made with government support under MH085687 awarded by National Institutes of Health. The government has certain rights in the invention." and insert --This invention was made with government support under Grant No. MH085687, Grant No. MH084512, and Grant No. HG005031 awarded by the National Institutes of Health. The government has certain rights in the invention.--, therefor Signed and Sealed this
Twenty-ninth Day of March, 2016

Michelle K. Lee
*Director of the United States Patent and Trademark Office*